(12) United States Patent
Yang et al.

(10) Patent No.: US 9,409,122 B2
(45) Date of Patent: Aug. 9, 2016

(54) GAS CAPTURE PROCESS

(75) Inventors: Qi Yang, Wheelers Hill (AU); Susan N. James, Rowville (AU); Mathew John Ballard, Glen Waverly (AU); Mark Bown, Clayton North (AU); Paul Feron, Floraville (AU); Graeme Douglas Puxty, Mayfield (AU)

(73) Assignee: Commonwealth Scientific and Industrial Research Organisation (AU)

( * ) Notice: Subject to any disclaimer, the term of this patent is extended or adjusted under 35 U.S.C. 154(b) by 482 days.

(21) Appl. No.: 14/112,724

(22) PCT Filed: Apr. 18, 2012

(86) PCT No.: PCT/AU2012/000409
§ 371 (c)(1),
(2), (4) Date: Jan. 16, 2014

(87) PCT Pub. No.: WO2012/142668
PCT Pub. Date: Oct. 26, 2012

(65) Prior Publication Data
US 2014/0127103 A1   May 8, 2014

(30) Foreign Application Priority Data

Apr. 18, 2011 (AU) ................................ 2011901448

(51) Int. Cl.
| | | |
|---|---|---|
| *B01D 53/14* | (2006.01) | |
| *B01D 53/62* | (2006.01) | |
| *C07D 211/26* | (2006.01) | |
| *C07D 211/58* | (2006.01) | |

(52) U.S. Cl.
CPC ............ *B01D 53/62* (2013.01); *B01D 53/1475* (2013.01); *B01D 53/1493* (2013.01); *C07D 211/26* (2013.01); *C07D 211/58* (2013.01); *B01D 2252/20442* (2013.01); *Y02C 10/04* (2013.01); *Y02C 10/06* (2013.01); *Y02P 20/152* (2015.11)

(58) Field of Classification Search
None
See application file for complete search history.

(56) References Cited

U.S. PATENT DOCUMENTS 5,189,173 A    2/1993   Lai et al.

FOREIGN PATENT DOCUMENTS

| AU | 2010211074 A1 | 8/2010 |
|---|---|---|
| EP | 2 036 602 A1 | 3/2009 |

(Continued)

OTHER PUBLICATIONS

International Search Report and Written Opinion for International Patent Application No. PCT/AU2012/000109 (mailed Jun. 1, 2012).

(Continued)

*Primary Examiner* — Jonathan Johnson
*Assistant Examiner* — Anita Nassiri Motlagh
(74) *Attorney, Agent, or Firm* — Merchant & Gould P.C.

(57) ABSTRACT

A process for the capture of $CO_2$ from gas streams, the process including contacting a $CO_2$ containing gas stream with a compound including: a primary or non-sterically hindered secondary amine group and at least one tertiary amine or sterically hindered secondary amine group; wherein the primary or non-sterically hindered secondary amine and the nearest tertiary or sterically hindered secondary amine group are separated by a carbon chain including 3 or 4 carbon atoms and wherein the compound is a compound of Formula (I).

9 Claims, 3 Drawing Sheets

(56) References Cited

FOREIGN PATENT DOCUMENTS

| JP | 2006-150298 A | 6/2006 |
|---|---|---|
| WO | WO 2005/062882 A2 | 7/2005 |
| WO | WO 2007/018461 A1 | 2/2007 |
| WO | WO 2007/124136 A1 | 11/2007 |
| WO | WO 2008/049919 A2 | 5/2008 |
| WO | WO 2009/035407 A1 | 3/2009 |
| WO | WO 2010/016551 A1 | 2/2010 |

OTHER PUBLICATIONS

Database: Chemical Abstracts. Accession No. 2003-511337. 4-piperidinamine, 1-methyl- (Registry No. 41838-46-4) and 4-piperidinamine, N,1-dimethyl- (Registry No. 73579-08-5), 14 pages.

Database: Registry. Registry No. 1178771-04-4 (Entered Sep. 1, 2009), 4 pages.

Database: Registry. Registry No. 415916-91-5 (Entered May 15, 2002), 2 pages.

Database: Registry. Registry No. 1218458-11-7 (Entered Apr. 11, 2010), 4 pages.

Database: Registry. Registry No. 56709-51-4 (Entered Nov. 16, 1984), 4 pages.

Database: Registry. Registry No. 62751-62-6 (Entered Nov. 16, 1984), 3 pages.

Database: Registry. Registry No. 1072412-09-9 (Entered Nov. 13, 2008), 3 pages.

Database: Registry. Registry No. 126657-47-4 (Entered Apr. 20, 1990), 3 pages.

Database: Registry. Registry No. 864710-80-5 (Entered Oct. 7, 2005), 3 pages.

Database: Registry. Registry No. 875229-91-7 (Entered Feb. 26, 2006), 3 pages.

Database: Registry. Registry No. 793660-70-5 (Entered Dec. 7, 2004), 3 pages.

Database: Registry. Registry No. 1184199-64-1 (Entered Sep. 14, 2009), 3 pages.

Database: Registry. Registry No. 1220177-37-6 (Entered Apr. 25, 2010), 3 pages.

Database: Registry. Registry No. 50534-45-7 (Entered Nov. 16, 1984), 4 pages.

Database: Registry. Registry No. 42389-59-3 (Entered Nov. 16, 1984), 3 pages.

Database: Registry. Registry No. 1220168-31-9 (Entered Apr. 23, 2010), 3 pages.

Database: Registry. Registry No. 89850-72-6 (Entered Nov. 16, 1984), 4 pages.

Database: Registry. Registry No. 1098624-57-7 (Entered Feb. 1, 2009), 3 pages.

Database: Registry. Registry No. 1098627-74-7 (Entered Feb. 1, 2009), 3 pages.

Database: Registry. Registry No. 1083424-14-9 (Entered Dec. 12, 2008), 3 pages.

Database: Registry. Registry No. 1178341-90-6 (Entered Aug. 31, 2009), 3 pages.

Singh, P. et al. "Structure and activity relationships for amine-based $CO_2$ absorbents-II", *Chemical Engineering Research and Design*, 87: 135-144 (2009).

Singh, P. et al. "Structure and activity relationships for $CO_2$ regeneration from aqueous amine-based absorbents", *Process Safety and Environmental Protection*, 86: 347-359 (2008).

Newman, "Acid and Sour Gas Treating Processes," *Gulf Publishing Company*, Texas, (1995).

Abdel-Magid et al., "Reductive Amination of Aldehydes and Ketones with Sodium Triacetoxyborohydride. Studies on Direct and Indirect Reductive Amination Procedures," *J. Org. Chem.*, 61(11):3849-3862 (1996).

Yokoyama et al., Potent CCR4 antagonists: Synthesis, evaluation, and docking study of 2,4-eiaminoquinazolines, *Bioorganic & Medicinal Chemistry*, 16: 7968-7974 (2008).

Pham et al., "Synthesis and Evaluation of Novel Radioiodinated Benzamides for Malignant Melanoma," *J. Med. Chem.*, 50(15): 3561-3572 (2007).

Liu et al., "Simultaneous Deprotection and Purification of BOC-amines Based on Ionic Resin Capture," *J. Org. Chem.*, 63: 3471-3473 (1998).

Walker et al., "Application of Sodium Borohydride Reduction to Synthesis of Substituted Aminopiperidines, Aminopiperazines, Aminopyridines, and Hydrazines," *J. Org. Chem.*, 26(8): 2740-2747 (1961).

Ito et al., "Practical Synthesis of Low-Density Lipoprotein Receptor Upregulator, N-[1-(3-Phenylpropane-1-yl)piperidin-4-yl]-5-thia-1,8b-diazaacenaphthylene-4-carboxamide," *Org. Proc. Res. Dev.*, 6(3): 238-241 (2002).

Pederson et al., "Dry Column Vacuum Chromatography," *Synthesis*, 16: 2431-2434 (2001).

Extended European Search Report for European Patent Application No. 12773962.1 (mailed Aug. 26, 2014).

Manetti et al., "[$^{35}$S]GTPγS binding studies of amphiphilic drugs-activated Gi proteins: A caveat," *Bioorganic & Medicinal Chemistry Letters*, 19(8): 2224-2229 (2009).

Fedi et al., "Discovery of a New Series of Potent and Selective Linear Tachykinin $NK_2$ Receptor Antagonists." *Journal of Medicinal Chemistry*, 50(20): 4793-4807 (2007).

López-Rodríguez et al., "Benzimidazole Derivatives. Part 1: Synthesis and Structure-Activity Relationships of New Benzimidazole-4-carboxamides and Carboxyiates as Potent and Selective 5-$HT_4$ Receptor Antagonists," *Bioorganic & Medicinal Chemistry*, 7: 2271-2281 (1999).

Engel et al., "Tricyclic Compounds as Selective Muscarinic Receptor Antagonists. 3. Structure-Selectivity Relationships in a Series of Cardioselective ($M_2$) Antimuscarinics," *Journal of Medicinal Chemistry*, 32(8): 1718-1724 (1989).

Sun et al., "Discovery of 5-[5-Fluoro-2-oxo-1,2-dihydroindol-(3Z)-ylidenemethyl]-2,4-dimethyl-1H-pyrrole-3-carboxylic Acid (2-Diethylaminoethyl)amide, a Novel Tyrosine Kinase Inhibitor Targeting Vascular Endothelial and Platelet-Derived Growth Factor Receptor Tyrosine Kinase," *Journal of Medicinal Chemistry*, 46(7): 1116-1119 (2003).

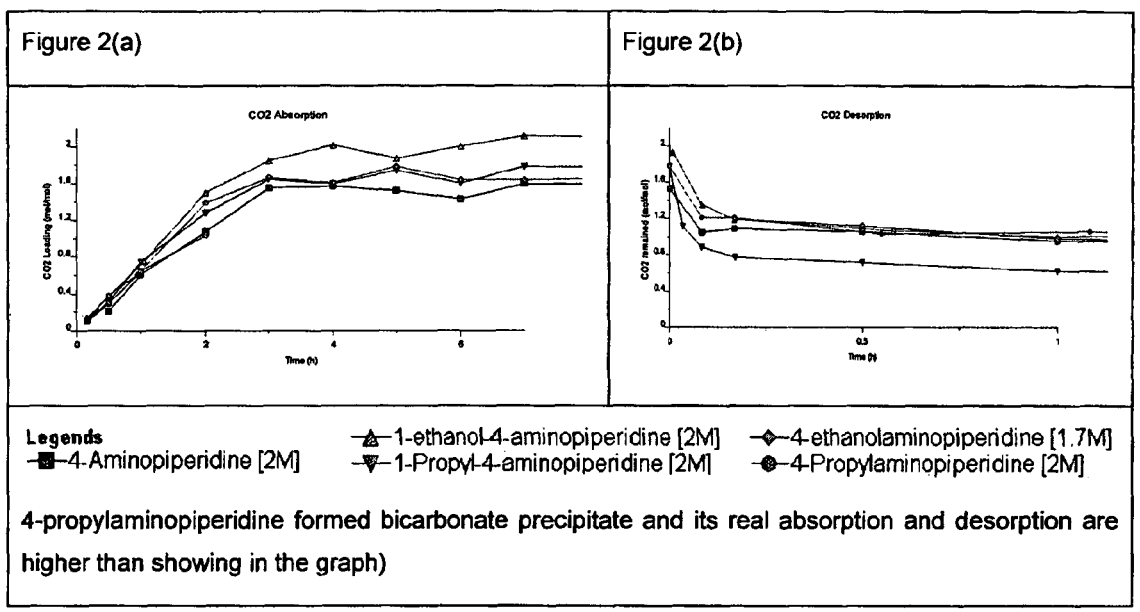

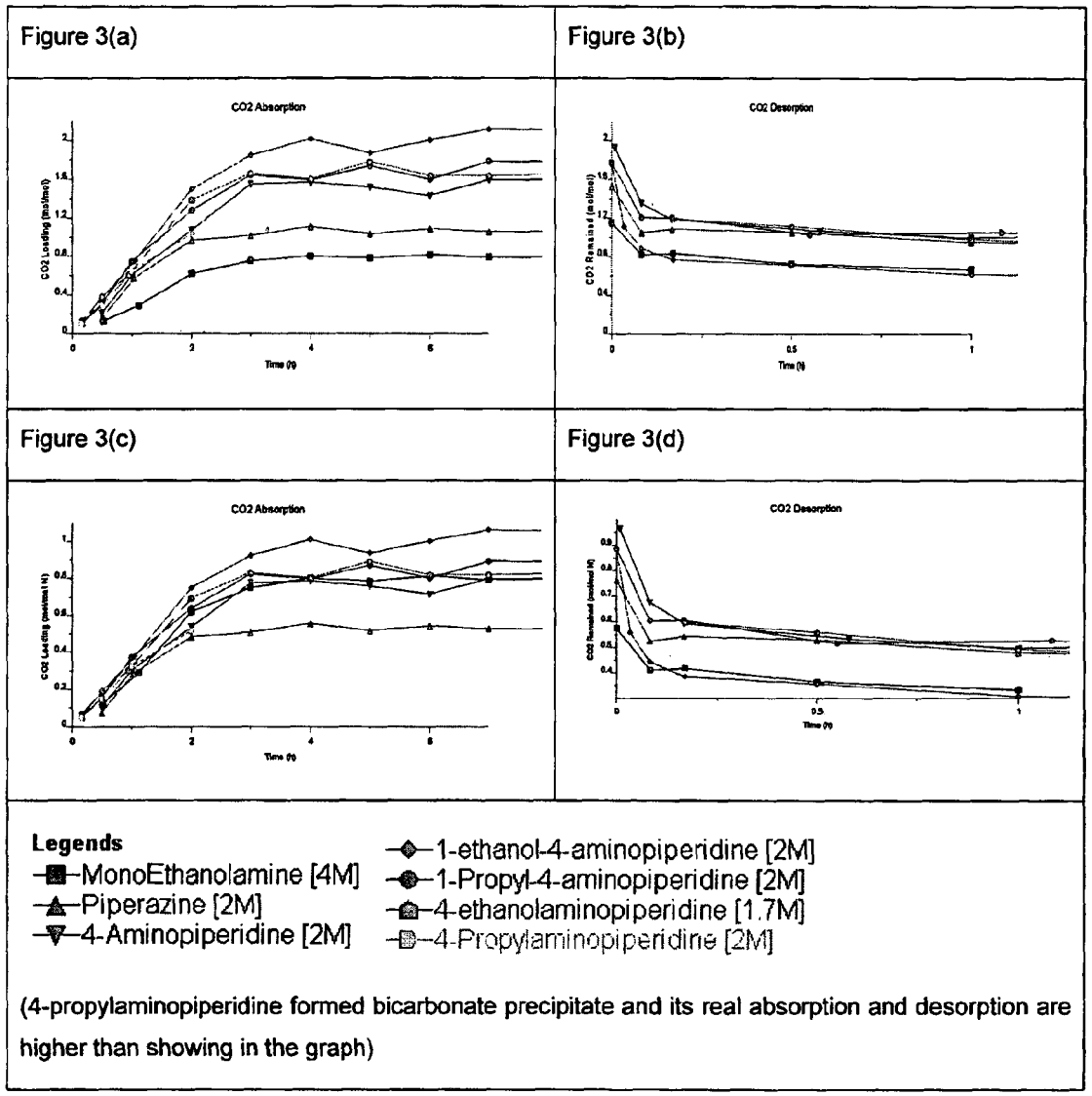

GAS CAPTURE PROCESS

This application is a U.S. National Stage Application under 35 U.S.C. §371 of International Patent Application No. PCT/AU2012/000409 filed 18 Apr. 2012, which claims the benefit of priority to Australian Patent Application No. 2011901448 filed 18 Apr. 2011, the disclosures of all of which are incorporated by reference herein in their entireties. The International Application was published in English on 26 Oct. 2012 as WO 2012/142668. To the extent appropriate, a claim of priority is made to each of the above disclosed applications.

FIELD OF THE INVENTION

This invention relates to amines and their use in capturing carbon dioxide from gas streams.

BACKGROUND OF THE INVENTION

There is growing pressure for stationary producers of greenhouse gases to dramatically reduce their atmospheric emissions. Of particular concern is the emission of carbon dioxide ($CO_2$) into the atmosphere. One method of reducing atmospheric $CO_2$ emissions is through its capture at a point source and subsequent storage in geological or other reservoirs.

The process for capturing $CO_2$ from power station and other combustion device flue gases is termed post combustion capture (PCC). In post combustion capture, the $CO_2$ in flue gas is first separated from nitrogen and residual oxygen using a suitable solvent in an absorber. The solvent is usually an aqueous basic mixture containing components that undergo a chemical reaction with acid gases such as $CO_2$. It might contain amines (e.g. alkanolamines, ammonia, alkylamines) and/or inorganic salts (e.g. carbonate or phosphate). The $CO_2$ is subsequently removed from the solvent in a process called stripping (or regeneration), thus allowing the solvent to be reused. The stripped $CO_2$ is liquefied by compression and cooling, with appropriate drying steps to prevent hydrate formation. PCC in this form is applicable to a variety of stationary $CO_2$ sources including power stations, steel plants, cement kilns, calciners and smelters.

Acid gases, such as carbon dioxide, are also present in natural gas and other pressurised gas streams and need to be removed to meet gas quality specifications. Pressurised gas streams containing $CO_2$ are also produced in fuel conversion processes such as natural gas reforming and coal gasification combined with a water-gas shift conversion to produce mixtures of hydrogen and carbon dioxide. These gas streams are then suitable for pre-combustion capture of $CO_2$. The conventional approaches for such removal include membrane separation or amine treatment.

When $CO_2$ is absorbed into an aqueous solution a number of reactions can occur. The reactions are shown by the following equations where (1) is hydration of gaseous $CO_2$, (2) is the reaction of $CO_2$ with water to form carbonic acid, (3) is the reaction of $CO_2$ with hydroxide to form bicarbonate and (4) and (5) are the carbonic acid-bicarbonate-carbonate acid-base equilibria.

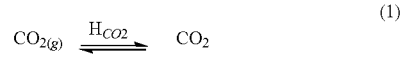

(1)

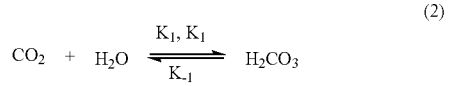

(2)

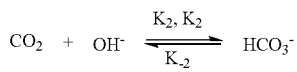

(3)

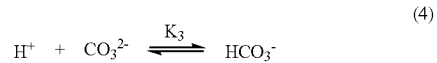

(4)

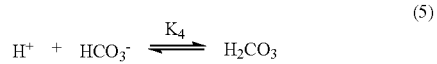

(5)

If an amine, or multiple amines, are present in solution a number of additional reactions may occur. If the amine is a sterically free primary or secondary amine such as monoethanolamine (MEA) or diethanolamine (DEA) the following reactions can occur between $CO_2$ and each amine. Equation (6) is the formation of a carbamate species via a nitrogen-carbon bond formation between the amine and $CO_2$. This is generally the kinetically fastest reaction of those that occur with $CO_2$. Equation (7) is the amine acid-base equilibrium. For polyamines the reactions of equation (6) and (7) may occur for each nitrogen atom. For sterically hindered primary or secondary amines the carbamate species is less stable than in sterically free amines which leads to enhanced formation of the bicarbonate species. For tertiary amines only the acid-base equilibrium of equation (7) occurs.

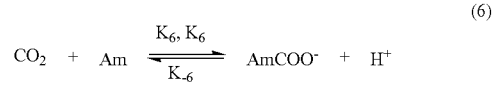

(6)

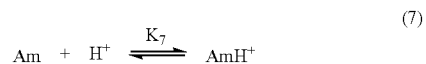

(7)

Monoethanolamine (MEA) is currently employed in industrial $CO_2$ capture but has a number of limitations, including solvent degradation due to oxidation and reaction with nitrogen and sulphur oxides, solvent losses due to high volatility and high energy requirements needed to desorb the $CO_2$ from the $CO_2$ loaded MEA. Some other amines used for industrial $CO_2$ capture have a larger $CO_2$ absorption capacity than MEA, but have poor rates of $CO_2$ capture. Slow $CO_2$ absorption rates are undesirable because to achieve the requisite absorption of $CO_2$, longer contact times between the $CO_2$ containing gas stream and the amine means that longer absorption columns and larger capital costs are usually required.

The use of amines as sorbents in $CO_2$ capture may be limited by the thermal degradation and oxidation of the amines. Much of the research on amine solvents for $CO_2$ capture is based around formulation with commercially available amines. There appears to be little study of novel amines that are designed, via amine structural modification, to match the characteristic requirement of $CO_2$ capture. 4-Aminopiperidine has been reported to perform well in $CO_2$ capture (Singh et al., 2008).

In addition, European patent application no 2036602 (Mitsubishi Heavy Industries, Ltd.) relates to an absorbent liquid for removing $CO_2$ and/or $H_2S$ from gas which includes compounds which are described in very general terms in the application (for example, by way of very broad general formulae). However, the data in the application showing the $CO_2$ absorption capacity of the compounds is quite limited.

However, there still exists a need for a more efficient $CO_2$ capture technology or process for post combustion capture.

It is an object of the present invention to overcome or at least alleviate one or more of the problems associated with the prior art.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The Applicants have surprisingly discovered that the compounds of the invention (as represented by formula (I) below) exhibit good molar $CO_2$ cyclic capacities. The compounds of formula (I), which are derivatives of 4-aminopiperidine, show a higher molar $CO_2$ cyclic capacity that that of 4-aminopiperidine itself.

Accordingly, in one aspect, the present invention provides a process for the capture of $CO_2$ from gas streams, the process including contacting a $CO_2$ containing gas stream with a compound including:
  a primary or non-sterically hindered secondary amine group and
  at least one tertiary amine or sterically hindered secondary amine group;
wherein the primary or non-sterically hindered secondary amine and the nearest tertiary or sterically hindered secondary amine group are separated by a carbon chain including 3 or 4 carbon atoms and wherein the compound is a compound of Formula (I)

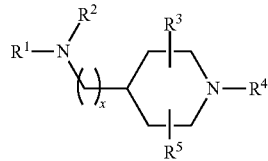

(I)

wherein
$R^1$ is represented by hydrogen, $C_2$ to $C_6$ alkanol or $C_1$ to $C_6$ alkyl;
$R^2$ is represented by hydrogen, $C_1$ to $C_6$ alkyl, $C_2$ to $C_6$ alkanol, —$(CH_2)_n$—$NR_6R_7$, —$(CH_2)_p$—COOH, —$(CH_2)_p$COOQ, —$(CH_2)_p$-heterocyclic ring containing one to four heteroatoms independently selected from nitrogen, oxygen and sulphur;
$R^3$ and $R^5$ are independently selected from hydrogen, $C_1$ to $C_4$ alkyl, $C_2$ to $C_6$ alkanol, —$(CH_2)_n$—$NR^8R^9$;
$R^4$ is represented by hydrogen, $C_1$ to $C_6$ alkyl, $C_2$ to $C_6$ alkanol, —$(CH_2)_n$—$NR_6R_7$, —$(CH_2)_p$—COOH, —$(CH_2)_p$COOQ, —$(CH_2)_p$—$SO_3H$, —$(CH_2)_p SO_3Q$, —$(CH_2)_p$—$PO_3H_2$, —$(CH_2)_p PO_3Q_s$, —$(CH_2)_p$-heterocyclic ring containing one to four heteroatoms independently selected from nitrogen, oxygen and sulphur;
x is 0 or 1;
n is 2 to 6;
p is 1 to 6;
Q is hydrogen, a metal ion or $R^{16}R^{17}R^{18}R^{19}N^+$;
s is 1 or 2
$R^6$ and $R^7$ are independently selected from hydrogen, alkyl, alkanol, alkylamine or $R^6$ and $R^7$ together with the nitrogen atom to which they are attached form a ring structure $R^8$ and $R^9$ are independently selected from $C_1$ to $C_6$ alkyl, $C_2$ to $C_6$ alkanol, $C_2$ to $C_6$ alkylamine, —$(CH_2)_n$—$NR_6R_7$, —$(CH_2)_p$—COOH, —$(CH_2)_p$COOQ, —$(CH_2)_p$—$SO_3H$, —$(CH_2)_p SO_3Q$, —$(CH_2)_p$—$PO_3H_2$, —$(CH_2)_p PO_3Q_s$, or $R^8$ and $R^9$ together with the nitrogen atom to which they are attached form a ring structure; and
$R^{16}, R^{17}, R^{18}$ and $R^{19}$ are independently selected from hydrogen or alkyl;
with the proviso that when $R^4$ is hydrogen, $R^1$ and/or $R^2$ is not hydrogen;
when $R^4$ is not hydrogen, $R^1$ and/or $R^2$ is hydrogen;
when $R^4$ and $R^1$ are both hydrogen, $R^2$ is not methyl; and
when $R^4$ and $R^2$ are both hydrogen, $R^1$ is not methyl.

In a further aspect, the present invention provides a compound including:
  a primary or non-sterically hindered secondary amine group and
  at least one tertiary amine or a sterically hindered secondary amine group;
wherein the primary or non-sterically hindered secondary amine group and the nearest tertiary or sterically hindered secondary amine group are separated by a carbon chain including 3 or 4 carbon atoms; and
wherein the compound is a compound of Formula (I):

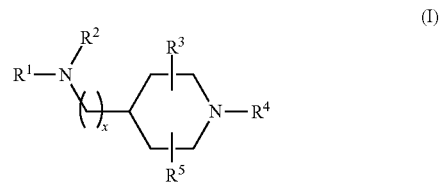

(I)

wherein
$R^1$ is represented by hydrogen, $C_2$ to $C_6$ alkanol or $C_1$ to $C_6$ alkyl;
$R^2$ is represented by hydrogen, $C_1$ to $C_6$ alkyl, $C_2$ to $C_6$ alkanol, —$(CH_2)_n$—$NR_6R_7$, —$(CH_2)_p$—COOH, —$(CH_2)_p$COOQ, —$(CH_2)_p$-heterocyclic ring containing one to four heteroatoms independently selected from nitrogen, oxygen and sulphur;
$R^3$ and $R^5$ are independently selected from hydrogen, $C_1$ to $C_4$ alkyl, $C_1$ to $C_4$ alkanol, —$(CH_2)_p$—$NR^8R^9$;
$R^4$ is represented by hydrogen, $C_1$ to $C_6$ alkyl, $C_2$ to $C_6$ alkanol, —$(CH_2)_n$—$NR^6R^7$, —$(CH_2)_p$—COOH, —$(CH_2)_p$COOQ, —$(CH_2)_p$—$SO_3H$, —$(CH_2)_p SO_3Q$, —$(CH_2)_p$—$PO_3H_2$, —$(CH_2)_p PO_3Q_s$, —$(CH_2)_p$-heterocyclic ring containing one to four heteroatoms independently selected from nitrogen, oxygen and sulphur;
x is 0 or 1;
n is 2 to 6;
p is 1 to 6;
Q is hydrogen, a metal ion or $R^{16}R^{17}R^{18}R^{19}N^+$;
s is 1 or 2;
$R^6$ and $R^7$ are independently selected from hydrogen, $C_1$ to $C_6$ alkyl, $C_2$ to $C_6$ alkanol, $C_2$ to $C_6$ alkylamine or $R^6$ and $R^7$ together with the nitrogen atom to which they are attached form a ring structure
$R^8$ and $R^9$ are independently selected from $C_1$ to $C_6$ alkyl, $C_2$ to $C_6$ alkanol, $C_2$ to $C_6$ alkylamine, —$(CH_2)_n$—$NR_6R_7$, —$(CH_2)_p$—COOH, —$(CH_2)_p$COOQ, —$(CH_2)_p$—$SO_3H$, —$(CH_2)_p SO_3Q$, —$(CH_2)_p$—$PO_3H_2$, —$(CH_2)_p PO_3\%$, or $R^8$ and $R^9$ together with the nitrogen atom to which they are attached form a ring structure;

$R^{14}$ and $R^{15}$ are independently selected from $C_1$ to $C_6$ alkyl, $C_2$ to $C_6$ alkanol, $C_2$ to $C_6$ alkylamine or $R^{14}$ and $R^{15}$ together with the nitrogen atom to which they are attached form a ring structure; and $R^{16}$, $R^{17}$, $R^{18}$ and $R^{19}$ are independently selected from hydrogen or alkyl;

with the proviso that when $R^4$ is hydrogen, $R^1$ and/or $R^2$ is not hydrogen;

when $R^4$ is not hydrogen, $R^1$ and/or $R^2$ is hydrogen;

when $R^4$ and $R^1$ are both hydrogen, $R^2$ is not methyl; and when $R^4$ and $R^2$ are both hydrogen, $R^1$ is not methyl.

BRIEF DESCRIPTION OF THE DRAWINGS/FIGURES

FIG. 2 shows the $CO_2$ absorption and desorption of 1-ethanol-4-aminopiperidine, 1-propyl-4-aminopiperidine, 4-ethanolaminopiperidine, 4-propylaminopiperidine compared with 4-aminopiperidine.

FIG. 3 shows the $CO_2$ absorption and desorption of 1-ethanol-4-aminopiperidine, 1-propyl-4-aminopiperidine, 4-ethanolaminopiperidine, 4-propylaminopiperidine, 4-aminopiperidine compared with monoethanolamine and piperazine.

DETAILED DESCRIPTION OF THE EMBODIMENTS

Figure 1:
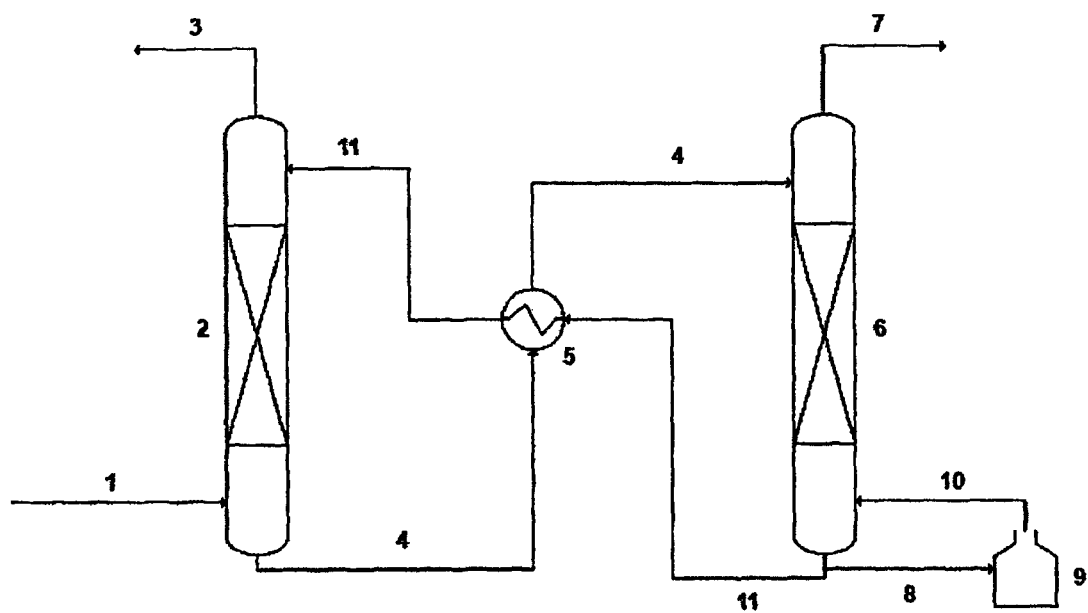
FIG. 1 shows a flow-diagram example of a $CO_2$ capture apparatus that may be employed in the process of one embodiment of the present invention.

As used herein, the term "sterically hindered secondary amine" means that the substituent on the secondary amine has sufficient bulk such that a reaction between the secondary amine and $CO_2$ produces an unstable carbamate species.

As used herein, the term "alkyl" means a straight or branched chain, or cyclic, saturated aliphatic group, or a combination thereof.

As used herein, the term "alkanol" means a group where an alcohol group (—OH) is bound to a carbon atom, ie, —$(CH_2)_n$OH.

As used herein, the term "alkylamine" means a group where an alkyl group is bound to the nitrogen atom of an amine group.

As used herein, except where the context requires otherwise, the term "comprise" and variations of the term, such as "comprising", "comprises" and "comprised", are not intended to exclude further additives, components, integers or steps.

It has surprisingly been found that the compounds used in the process of the present invention, described above, have a higher capacity for $CO_2$ absorption and good reaction rates in $CO_2$ absorption, and higher efficiency in $CO_2$ desorption.

In addition, the compounds have relatively high boiling points which may result in reduced amine evaporation during the process. The reduction in evaporation may be beneficial from cost and environmental impact perspectives.

In one embodiment the present invention provides a compound of Formula (I)

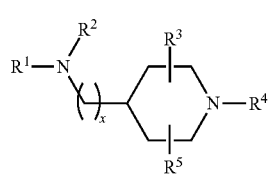

(I)

wherein $R^1$ is represented by hydrogen, $C_2$ to $C_6$ alkanol or $C_1$ to $C_6$ alkyl;

$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);

$R^3$ and $R^5$ are independently selected from hydrogen, $C_1$ to $C_4$ alkyl and $C_1$ to $C_4$ alkanol;

$R^4$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole); and x is 0 or 1;

with the proviso that when $R^4$ is hydrogen, $R^2$ is not hydrogen;

when $R^2$ is hydrogen, $R^4$ is not hydrogen; and when $R^2$ is hydrogen, $R^1$ is hydrogen and x is 0.

In a further embodiment, the present invention provides a compound of Formula (I) wherein:

x is 0 or 1;

$R^1$ is represented by hydrogen or $C_1$ alkyl;

$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);

$R^3$ is represented by hydrogen;

$R^4$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole); and $R^5$ is represented by hydrogen;

with the proviso that when $R^4$ is hydrogen, $R^2$ is not hydrogen;

when $R^2$ is hydrogen, $R^4$ is not hydrogen; and when $R^2$ is hydrogen, $R^1$ is hydrogen and x is 0.

In a further embodiment, the present invention provides a compound of Formula (I) wherein:

x is 0 or 1;

$R^1$ is represented by hydrogen or $C_1$ alkyl;

$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);

$R^3$ is represented by hydrogen;

$R^4$ is represented by hydrogen; and $R^5$ is represented by hydrogen.

In a further embodiment, the present invention provides a compound of Formula (I) wherein:

x is 0;

$R^1$ is represented by hydrogen;

$R^2$ is represented by hydrogen;

$R^3$ is represented by hydrogen;
$R^4$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole); and
$R^5$ is represented by hydrogen.

In a still further embodiment, the present invention provides a compound of Formula (I) wherein:
x is 0 or 1;
$R^1$ is represented by hydrogen or $C_1$ alkyl;
$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen;
with the proviso that when x is 0, $R^1$ is hydrogen.

In a still further embodiment, the present invention provides a compound of Formula (I) wherein:
x is 0;
$R^1$ is represented by hydrogen;
$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a compound of Formula (I) wherein:
x is 0;
$R^1$ is represented by $C_1$ alkyl;
$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a compound of Formula (I) wherein:
x is 0;
$R^1$ is represented by hydrogen;
$R^2$ is represented by hydrogen;
$R^3$ is represented by hydrogen;
$R^4$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole); and
$R^5$ is represented by hydrogen.

In a still further embodiment, the present invention provides a compound of Formula (I) wherein:
x is 1;
$R^1$ is represented by hydrogen;
$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a compound of Formula (I) wherein:
x is 1;
$R^1$ is represented by $C_1$ alkyl;
$R^2$ is represented by hydrogen, —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a compound of Formula (I) wherein:
x is 0;
$R^1$ is represented by $C_1$ alkyl;
$R^2$ is represented by —$CH_2CH_2CH_3$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a compound of Formula (I) wherein:
x is 0;
$R^1$ is represented by hydrogen;
$R^2$ is represented by hydrogen;
$R^3$ is represented by hydrogen;
$R^4$ is represented by —$CH_2CH_3$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole); and
$R^5$ is represented by hydrogen.

In a still further embodiment, the present invention provides a compound of Formula (I) wherein:
x is 0 or 1;
$R^1$ is represented by hydrogen or $C_1$ alkyl;
$R^2$ is represented by —$CH_2CH_3$, —$CH_2CH_2CH_3$, —$(CH_2)_2OH$, —$(CH_2)_3OH$, —$(CH_2)_6OH$, —$CH_2COOH$ or —$(CH_2)_2N(CH_3)_2$;
$R^3$ is represented by hydrogen;
$R^4$ is represented by hydrogen; and
$R^5$ is represented by hydrogen.

In a still further embodiment, the present invention provides a compound of Formula (I) wherein:
x is 0;
$R^1$ is represented by hydrogen;
$R^2$ is represented by —$CH_2CH_3$, —$(CH_2)_2OH$, —$(CH_2)_3OH$, —$(CH_2)_6OH$ or —$(CH_2)_2N(CH_3)_2$;
$R^3$ is represented by hydrogen;
$R^4$ is represented by hydrogen; and
$R^5$ is represented by hydrogen.

In a still further embodiment, the present invention provides a compound of Formula (I) wherein:
x is 0;
$R^1$ is represented by $C_1$ alkyl;
$R^2$ is represented by —$CH_2CH_3$, —$(CH_2)_2OH$, —$(CH_2)_3OH$ or —$(CH_2)_6OH$;
$R^3$ is represented by hydrogen;
$R^4$ is represented by hydrogen; and
$R^5$ is represented by hydrogen.

In a still further embodiment, the present invention provides a compound of Formula (I) wherein:
x is 1;
$R^1$ is represented by hydrogen;

$R^2$ is represented by —CH$_2$CH$_3$, —(CH$_2$)$_2$OH, —(CH$_2$)$_6$OH or —CH$_2$COOH;
$R^3$ is represented by hydrogen;
$R^4$ is represented by hydrogen; and
$R^5$ is represented by hydrogen.

In a still further embodiment, the present invention provides a compound of Formula (I) wherein:
x is 1;
$R^1$ is represented by C$_1$ alkyl;
$R^2$ is represented by —CH$_2$CH$_3$ or —(CH$_2$)$_2$OH;
$R^3$ is represented by hydrogen;
$R^4$ is represented by hydrogen; and
$R^5$ is represented by hydrogen.

In a still further embodiment, the present invention provides a compound of Formula (I) wherein:
x is 0 or 1;
$R^1$ is represented by hydrogen;
$R^2$ is represented by hydrogen;
$R^3$ is represented by hydrogen;
$R^4$ is represented by —CH$_2$CH$_3$, —CH$_2$CH$_2$CH$_3$, —(CH$_2$)$_2$OH, —(CH$_2$)$_3$OH or —(CH$_2$)$_6$OH; and
$R^5$ is represented by hydrogen.

In a further embodiment, the present invention provides a compound of Formula (I) wherein:
x is 0 or 1;
$R^1$ is represented by hydrogen or C$_1$ alkyl;
$R^2$ is represented by hydrogen, —CH$_2$CH$_3$, —CH$_2$CH$_2$CH$_3$ or —(CH$_2$)$_2$N(CH$_3$)$_2$;
$R^3$ is represented by hydrogen;
$R^4$ is represented by hydrogen, —CH$_2$CH$_3$, —CH$_2$CH$_2$CH$_3$ or —(CH$_2$)$_2$N(CH$_3$)$_2$; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a further embodiment, the present invention provides a compound of Formula (I) wherein:
x is 0 or 1;
$R^1$ is represented by hydrogen or C$_1$ alkyl;
$R^2$ is represented by hydrogen, —(CH$_2$)$_2$OH, —(CH$_2$)$_3$OH, —(CH$_2$)$_6$OH, —CH$_2$COOH, —CH$_2$COONa or —CH$_2$COOK;
$R^3$ is represented by hydrogen;
$R^4$ is represented by hydrogen, —(CH$_2$)$_2$OH, —(CH$_2$)$_3$OH, —(CH$_2$)$_6$OH, —CH$_2$COOH, —CH$_2$COONa or —CH$_2$COOK; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, R' is hydrogen and x is 0.

In a further embodiment, the present invention provides a compound of Formula (I) wherein:
x is 0 or 1;
$R^1$ is represented by hydrogen or C$_1$ alkyl;
$R^2$ is represented by hydrogen, —(CH$_2$)$_2$OH, —(CH$_2$)$_3$OH or —(CH$_2$)$_6$OH;
$R^3$ is represented by hydrogen;
$R^4$ is represented by hydrogen, —(CH$_2$)$_2$OH, —(CH$_2$)$_3$OH or —(CH$_2$)$_6$OH; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a further embodiment, the present invention provides a compound of Formula (I) wherein:
x is 0 or 1;
$R^1$ is represented by hydrogen or C$_1$ alkyl;
$R^2$ is represented by hydrogen, —CH$_2$COOH, —CH$_2$COONa or —CH$_2$COOK;
$R^3$ is represented by hydrogen;
$R^4$ is represented by hydrogen, —CH$_2$COOH, —CH$_2$COONa or —CH$_2$COOK; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a further embodiment, the present invention provides a compound of Formula (I) wherein:
x is 0 or 1;
$R^1$ is represented by hydrogen or C$_1$ alkyl;
$R^2$ is represented by hydrogen, —(CH$_2$)$_2$N(CH$_2$CH$_2$)$_2$O, —(CH$_2$)$_2$N(CH$_2$CH$_2$)$_2$S, —CH$_2$(5-imidazole) or —(CH$_2$)$_2$(5-imidazole);
$R^3$ is represented by hydrogen;
$R^4$ is represented by hydrogen, —(CH$_2$)$_2$N(CH$_2$CH$_2$)$_2$O, —(CH$_2$)$_2$N(CH$_2$CH$_2$)$_2$S, —CH$_2$(5-imidazole) or —(CH$_2$)$_2$(5-imidazole); and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a still further embodiment, the present invention provides a compound of Formula (I) wherein:
x is 0 or 1;
$R^1$ is represented by hydrogen;
$R^2$ is represented by ethyl, propyl or —(CH$_2$)$_2$N(CH$_3$)$_2$;
$R^3$ is represented by hydrogen;
$R^4$ is represented by hydrogen; and
$R^5$ is represented by hydrogen.

In a further embodiment, the present invention provides a compound selected from the group consisting of:

-continued
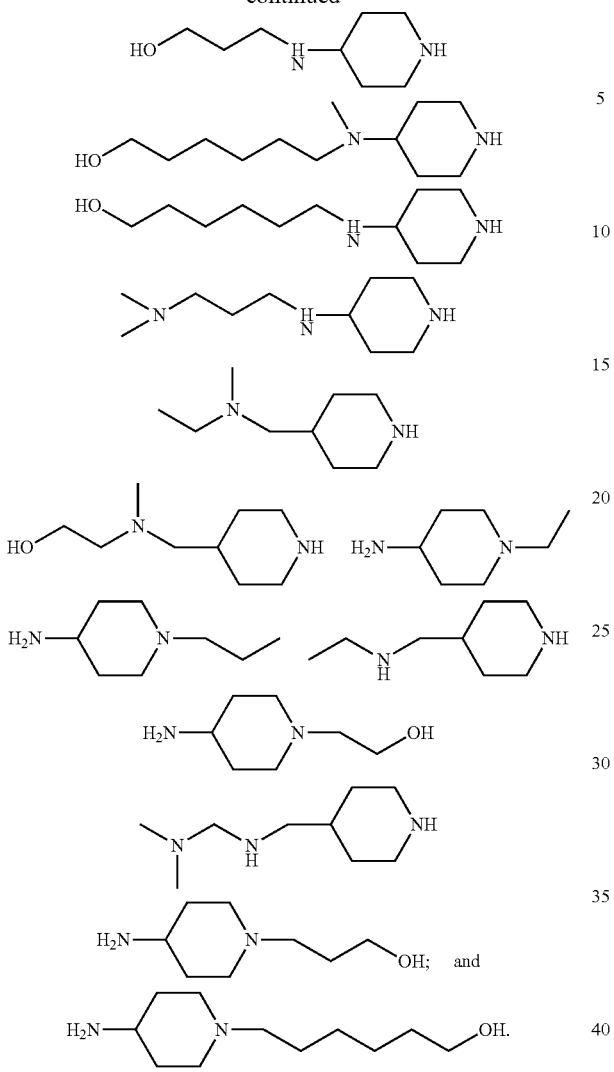
In a further embodiment, the present invention provides a compound selected from the group consisting of:
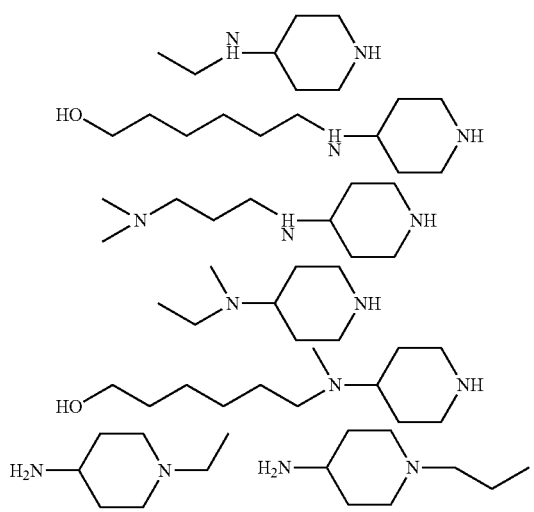
-continued
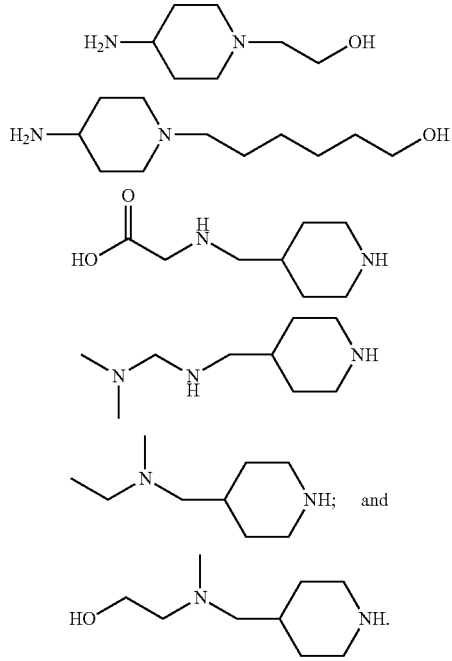
In a further embodiment, the present invention provides a compound selected from the group consisting of:
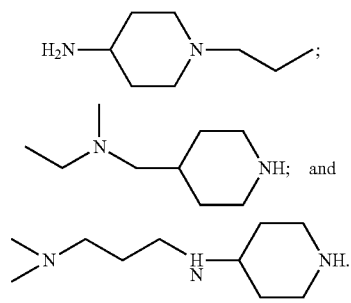
In a further embodiment, the present invention provides a compound selected from the group consisting of:
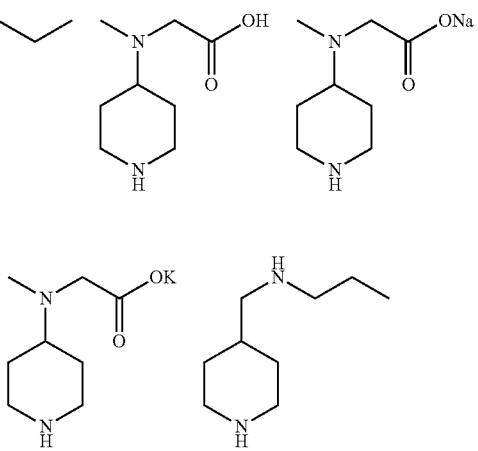

$R^1$ is represented by hydrogen, $C_2$ to $C_6$ alkanol or $C_1$ to $C_6$ alkyl;

$R^2$ is represented by hydrogen, $-CH_2CH_3$, $-CH_2CH_2CH_3$, $-(CH_2)_2OH$, $-(CH_2)_3OH$, $-(CH_2)_6OH$, $-CH_2COOH$, $-CH_2COONa$, $-CH_2COOK$, $-(CH_2)_2N(CH_3)_2$, $-(CH_2)_2N(CH_2CH_2)_2O$, $-(CH_2)_2N(CH_2CH_2)_2S$, $-CH_2$(5-imidazole) or $-(CH_2)_2$(5-imidazole);

$R^3$ and $R^5$ are independently selected from hydrogen, $C_1$ to $C_4$ alkyl and $C_1$ to $C_4$ alkanol;

$R^4$ is represented by hydrogen-$CH_2CH_3$, $-CH_2CH_2CH_3$, $-(CH_2)_2OH$, $-(CH_2)_3OH$, $-(CH_2)_6OH$, $-CH_2COOH$, $-CH_2COONa$, $-CH_2COOK$, $-(CH_2)_2N(CH_3)_2$, $-(CH_2)_2N(CH_2CH_2)_2O$, $-(CH_2)_2N(CH_2CH_2)_2S$, $-CH_2$(5-imidazole) or $-(CH_2)_2$(5-imidazole); and x is 0 or 1;

with the proviso that when $R^4$ is hydrogen, $R^2$ is not hydrogen;

when $R^2$ is hydrogen, $R^4$ is not hydrogen; and when $R^2$ is hydrogen, $R^1$ is hydrogen and x is 0.

In a further embodiment, the present invention provides a process wherein in the compound of Formula (I):

x is 0 or 1;

$R^1$ is represented by hydrogen or $C_1$ alkyl;

$R^2$ is represented by hydrogen, $-CH_2CH_3$, $-CH_2CH_2CH_3$, $-(CH_2)_2OH$, $-(CH_2)_3OH$, $-(CH_2)_6OH$, $-CH_2COOH$, $-CH_2COONa$, $-CH_2COOK$, $-(CH_2)_2N(CH_3)_2$, $-(CH_2)_2N(CH_2CH_2)_2O$, $-(CH_2)_2N(CH_2CH_2)_2S$, $-CH_2$(5-imidazole) or $-(CH_2)_2$(5-imidazole);

$R^3$ is represented by hydrogen;

$R^4$ is represented by hydrogen, $-CH_2CH_3$, $-CH_2CH_2CH_3$, $-(CH_2)_2OH$, $-(CH_2)_3OH$, $-(CH_2)_6OH$, $-CH_2COOH$, $-CH_2COONa$, $-CH_2COOK$, $-(CH_2)_2N(CH_3)_{21}$ $-(CH_2)_2N(CH_2CH_2)_2O$, $-(CH_2)_2N(CH_2CH_2)_2S$, $-CH_2$(5-imidazole) or $-(CH_2)_2$(5-imidazole); and $R^5$ is represented by hydrogen;

with the proviso that when $R^4$ is hydrogen, $R^2$ is not hydrogen;

when $R^2$ is hydrogen, $R^4$ is not hydrogen; and when $R^2$ is hydrogen, $R^1$ is hydrogen and x is 0.

In a further embodiment, the present invention provides a process wherein in the compound of Formula (I):

x is 0 or 1;

$R^1$ is represented by hydrogen or $C_1$ alkyl;

$R^2$ is represented by $-CH_2CH_3$, $-CH_2CH_2CH_3$, $-(CH_2)_2OH$, $-(CH_2)_3OH$, $-(CH_2)_6OH$, $-CH_2COOH$, $-CH_2COONa$, $-CH_2COOK$, $-(CH_2)_2N(CH_3)_2$, $-(CH_2)_2N(CH_2CH_2)_2O$, $-(CH_2)_2N(CH_2CH_2)_2S$, $-CH_2$(5-imidazole) or $-(CH_2)_2$(5-imidazole);

$R^3$ is represented by hydrogen;

$R^4$ is represented by hydrogen; and $R^5$ is represented by hydrogen.

In a further embodiment, the present invention provides a process wherein in the compound of Formula (I):

x is 0 or 1;

$R^1$ is represented by hydrogen;

$R^2$ is represented by hydrogen;

$R^3$ is represented by hydrogen;

$R^4$ is represented by $-CH_2CH_3$, $-CH_2CH_2CH_3$, $-(CH_2)_2OH$, $-(CH_2)_3OH$, $-(CH_2)_6OH$, $-CH_2COOH$, $-CH_2COONa$, $-CH_2COOK$, $-(CH_2)_2N(CH_3)_2$, $-(CH_2)_2N(CH_2CH_2)_2O$, $-(CH_2)_2N(CH_2CH_2)_2S$, $-CH_2$(5-imidazole) or $-(CH_2)_2$(5-imidazole); and $R^5$ is represented by hydrogen.

In a still further embodiment, the present invention provides a process wherein in the compound of Formula (I):
x is 0 or 1;
$R^1$ is represented by hydrogen or $C_1$ alkyl;
$R^2$ is represented by —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen;
with the proviso that when x is O, $R^1$ is hydrogen.

In a still further embodiment, the present invention provides a process wherein in the compound of Formula (I):
x is 0;
$R^1$ is represented by hydrogen;
$R^2$ is represented by —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a process wherein in the compound of Formula (I):
x is 0;
$R^1$ is represented by $C_1$ alkyl;
$R^2$ is represented by —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a process wherein in the compound of Formula (I):
x is 0;
$R^1$ is represented by hydrogen;
$R^2$ is represented by hydrogen;
$R^3$ is represented by hydrogen;
$R^4$ is represented by —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole) and
$R^5$ is represented by hydrogen.

In a still further embodiment, the present invention provides a process wherein in the compound of Formula (I):
x is 1;
$R^1$ is represented by hydrogen;
$R^2$ is represented by —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a process wherein in the compound of Formula (I):
x is 1;
$R^1$ is represented by $C_1$ alkyl;
$R^2$ is represented by —$CH_2CH_3$, —$CH_2CH_2CH_3$, —$(CH_2)_2OH$, —$(CH_2)_3OH$, —$(CH_2)_6OH$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a process wherein in the compound of Formula (I):
x is 0;
$R^1$ is represented by $C_1$ alkyl;
$R^2$ is represented by —$CH_2CH_2CH_3$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen; and
$R^5$ is represented by hydrogen.

In a still further embodiment, the present invention provides a process wherein in the compound of Formula (I):
x is 0;
$R^1$ is represented by hydrogen;
$R^2$ is represented by hydrogen;
$R^3$ is represented by hydrogen;
$R^4$ is represented by —$CH_2CH_3$, —$CH_2COOH$, —$CH_2COONa$, —$CH_2COOK$, —$(CH_2)_2N(CH_3)_2$, —$(CH_2)_2N(CH_2CH_2)_2O$, —$(CH_2)_2N(CH_2CH_2)_2S$, —$CH_2$(5-imidazole) or —$(CH_2)_2$(5-imidazole); and
$R^5$ is represented by hydrogen.

In a still further embodiment, the present invention provides a process wherein in the compound of Formula (I):
x is 0 or 1;
$R^1$ is represented by hydrogen or $C_1$ alkyl;
$R^2$ is represented by —$CH_2CH_3$, —$CH_2CH_2CH_3$, —$(CH_2)_2OH$, —$(CH_2)_3OH$, —$(CH_2)_6OH$, —$CH_2COOH$ or —$(CH_2)_2N(CH_3)_2$;
$R^3$ is represented by hydrogen;
$R^4$ is represented by hydrogen; and
$R^5$ is represented by hydrogen.

In a still further embodiment, the present invention provides a process wherein in the compound of Formula (I):
x is 0;
$R^1$ is represented by hydrogen;
$R^2$ is represented by —$CH_2CH_3$, —$(CH_2)_2OH$, —$(CH_2)_3OH$, —$(CH_2)_6OH$ or —$(CH_2)_2N(CH_3)_2$;
$R^3$ is represented by hydrogen;
$R^4$ is represented by hydrogen; and
$R^5$ is represented by hydrogen.

In a still further embodiment, the present invention provides a process wherein in the compound of Formula (I):
x is 0;
$R^1$ is represented by $C_1$ alkyl;
$R^2$ is represented by $CH_2CH_3$, —$(CH_2)_2OH$, —$(CH_2)_3OH$ or —$(CH_2)_6OH$;
$R^3$ is represented by hydrogen;
$R^4$ is represented by hydrogen; and
$R^5$ is represented by hydrogen.

In a still further embodiment, the present invention provides a process wherein in the compound of Formula (I):
x is 1;
$R^1$ is represented by hydrogen;
$R^2$ is represented by —$CH_2CH_3$, —$(CH_2)_2OH$, —$(CH_2)_6OH$ or —$CH_2COOH$;
$R^3$ is represented by hydrogen;
$R^4$ is represented by hydrogen; and
$R^5$ is represented by hydrogen.

In a still further embodiment, the present invention provides a process wherein in the compound of Formula (I):
x is 1;
$R^1$ is represented by $C_1$ alkyl;
$R^2$ is represented by —$CH_2CH_3$ or —$(CH_2)_2OH$;
$R^3$ is represented by hydrogen;
$R^4$ is represented by hydrogen; and
$R^5$ is represented by hydrogen.

In a still further embodiment, the present invention provides a process wherein in the compound of Formula (I):
x is 0;
$R^1$ is represented by hydrogen;
$R^2$ is represented by hydrogen;
$R^3$ is represented by hydrogen;
$R^4$ is represented by —$CH_2CH_3$, —$CH_2CH_2CH_3$, —$(CH_2)_2OH$, —$(CH_2)_3OH$ or —$(CH_2)_6OH$; and
$R^5$ is represented by hydrogen.

In a further embodiment, the present invention provides a process wherein in the compound of Formula (I):
x is 0 or 1;
$R^1$ is represented by hydrogen or $C_1$ alkyl;
$R^2$ is represented by hydrogen, —$CH_2CH_3$, —$CH_2CH_2CH_3$ or —$(CH_2)_2N(CH_3)_2$;
$R^3$ is represented by hydrogen;
$R^4$ is represented by hydrogen, —$CH_2CH_3$, —$CH_2CH_2CH_3$ or —$(CH_2)_2N(CH_3)_2$; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a further embodiment, the present invention provides a process wherein in the compound of Formula (I):
x is 0 or 1;
$R^1$ is represented by hydrogen or $C_1$ alkyl;
$R^2$ is represented by hydrogen, —$(CH_2)_2OH$, —$(CH_2)_3OH$, —$(CH_2)_6OH$, —$CH_2COOH$, —$CH_2COONa$ or —$CH_2COOK$;
$R^3$ is represented by hydrogen;
$R^4$ is represented by hydrogen, —$(CH_2)_2OH$, —$(CH_2)_3OH$, —$(CH_2)_6OH$, —$CH_2COOH$, —$CH_2COONa$ or —$CH_2COOK$; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a further embodiment, the present invention provides a process wherein in the compound of Formula (I):
x is 0 or 1;
$R^1$ is represented by hydrogen or $C_1$ alkyl;
$R^2$ is represented by hydrogen, —$(CH_2)_2OH$, —$(CH_2)_3OH$ or —$(CH_2)_6OH$;
$R^3$ is represented by hydrogen;
$R^4$ is represented by hydrogen, —$(CH_2)_2OH$, —$(CH_2)_3OH$ or —$(CH_2)_6OH$; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a further embodiment, the present invention provides a process wherein in the compound of Formula (I):
x is 0 or 1;
$R^1$ is represented by hydrogen or $C_1$ alkyl;
$R^2$ is represented by hydrogen, —$CH_2COOH$, —$CH_2COONa$ or —$CH_2COOK$;
$R^3$ is represented by hydrogen;
$R^4$ is represented by hydrogen, —$CH_2COOH$, —$CH_2COONa$ or —$CH_2COOK$; and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a further embodiment, the present invention provides a process wherein in the compound of Formula (I):
x is 0 or 1;
$R^1$ is represented by hydrogen or $C_1$ alkyl;
$R^2$ is represented by hydrogen, —$(CH_2)_2N(CH_2CH_2)_2O$, —$(CH_2)_2N(CH_2CH_2)_2S$, —$CH_2$(5-imidazole) or —$(CH_2)_2$(5-imidazole);
$R^3$ is represented by hydrogen;
$R^4$ is represented by hydrogen, —$(CH_2)_2N(CH_2CH_2)_2O$, —$(CH_2)_2N(CH_2CH_2)_2S$, —$CH_2$(5-imidazole) or —$(CH_2)_2$(5-imidazole); and
$R^5$ is represented by hydrogen;
with the proviso that when $R^4$ is hydrogen, $R^2$ is not hydrogen;
when $R^2$ is hydrogen, $R^4$ is not hydrogen; and
when $R^2$ is hydrogen, $R^1$ is hydrogen and x is 0.

In a still further embodiment, the present invention provides a process wherein, in the compound of Formula (I):
x is 0 or 1;
$R^1$ is represented by hydrogen;
$R^2$ is represented by ethyl, propyl or —$(CH_2)_2N(CH_3)_2$;
$R^3$ is represented by hydrogen;
$R^4$ is represented by hydrogen; and
$R^5$ is represented by hydrogen.

In a further embodiment, the present invention provides a process wherein in the compound of Formula (I) is selected from a group consisting of:

-continued

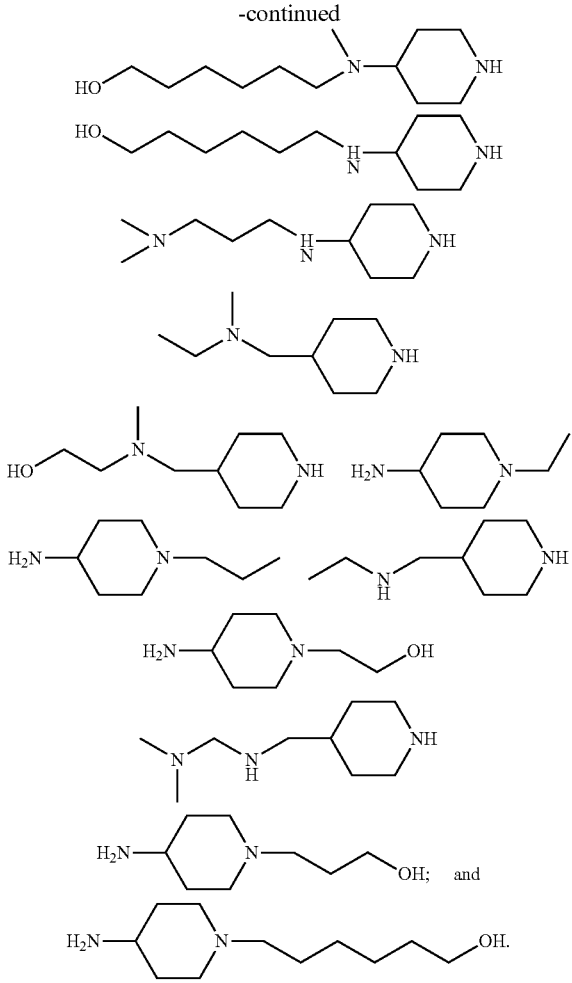

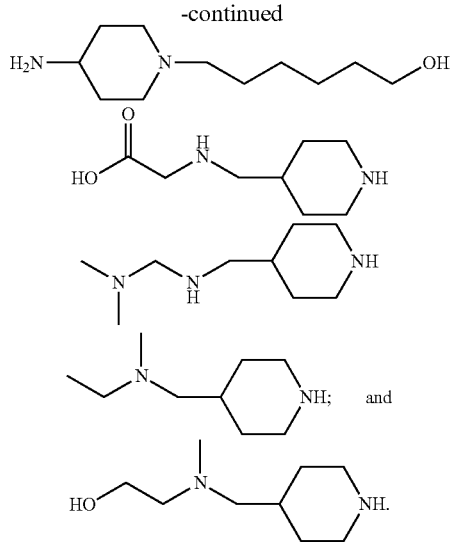

In a further embodiment, the present invention provides a process wherein in the compound of Formula (I) is selected from a group consisting of:

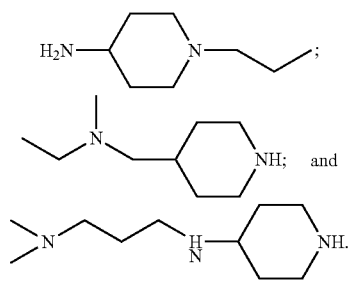

In a further embodiment, the present invention provides a process wherein in the compound of Formula (I) is selected from a group consisting of:

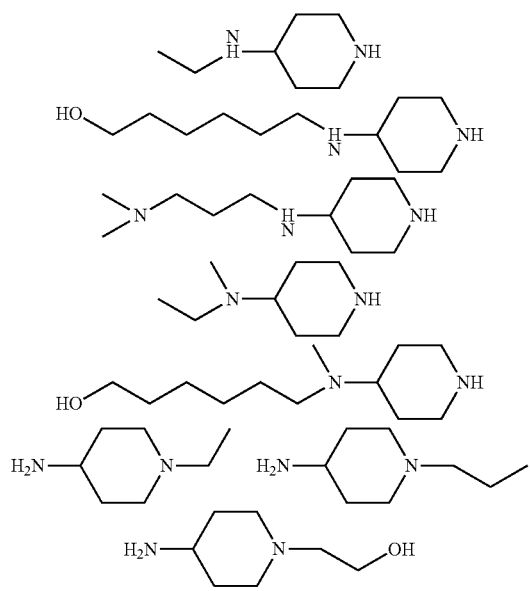

In a further embodiment, the present invention provides a process wherein in the compound of Formula (I) is selected from a group consisting of:

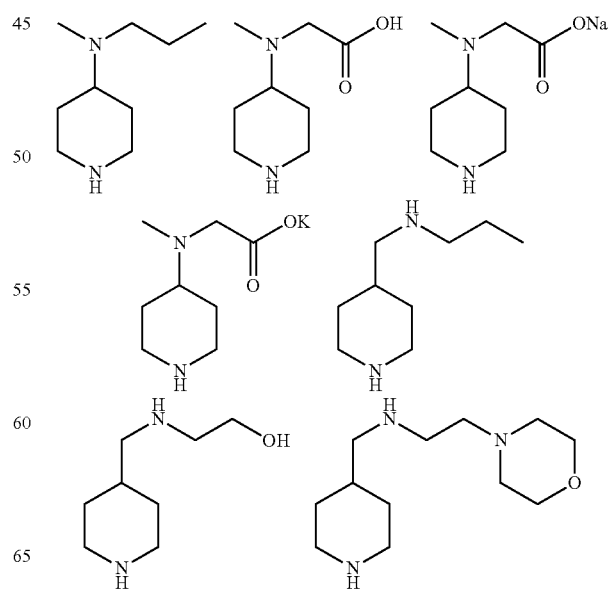

-continued

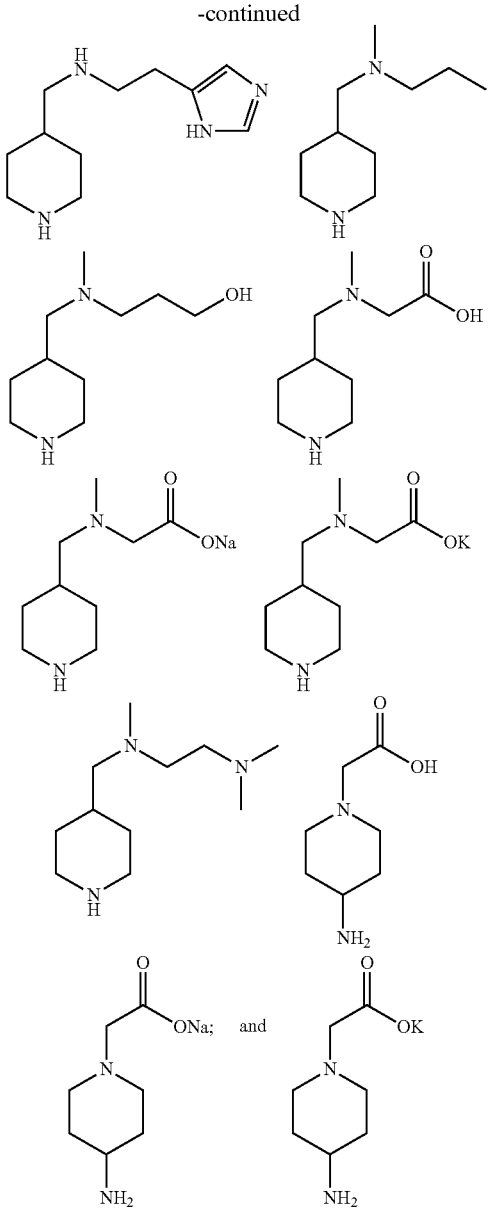

When a compound as described above is used in a mixture with another amine, (ie, a mixed amine solution), the $CO_2$ capture efficiency of the mixed amine solution is also better than that of 4-aminopiperidine used in a mixture with another amine. Without wishing to be bound by theory, it is thought that the compounds described above act as promoters in mixed amine solutions. Accordingly, the cost and energy consumption of $CO_2$ capture may be lowered by the use of a compound as described above, by itself, or in a mixture with another amine in $CO_2$ capture.

In the process of the present invention, the compound is typically present in the form of an aqueous solution. The compound may be present in the aqueous solution in an amount of from about 5 to 99 percent by weight, preferably from about 10 to 90 percent by weight, most preferably from about 15 to 75 percent by weight, based upon the total weight of the aqueous solution.

When the compound is used in a mixture with another amine, (ie, a mixed amine solution), the compound may be present in the mixed amine solution in an amount of from about 10 to 100 percent by weight, preferably from about 20 to 80 percent by weight, most preferably from about 30 to 70 percent by weight, based upon the total weight of the amine components.

The optimal amount of the compound used in the process of the present invention will depend upon the gas stream composition, outlet fluid requirement and circulation rate. A person skilled in the art would readily be able to determine the appropriate amount of the compound to use in the process of the present invention.

The process of the present invention may be carried out in conventional equipment for the removal of carbon dioxide from gas streams by reactive chemical absorption and detailed procedures are well known to the person skilled in the art. See, for example, the flow diagram of FIG. 1, or Newman, S. A., *Acid and Sour Gas Treating Processes*, Gulf Publishing Company, Texas, 1995.

In the embodiment described by FIG. 1, the equipment comprises an absorber column 2, a heat exchanger 5, a desorber column 6 and a reboiler 9. Flue gas, which typically comprises 1-15% $CO_2$, preferably 5-15% $CO_2$ and more preferably 10-15% $CO_2$, is optionally passed through a prescrubber and then passes through conduit 1 to the packed absorber column 2, where it is contacted with the compound of formula (I). Pressure and temperature conditions in the absorber column 2 are typically 1 atm and about 40 to 60° C. $CO_2$-lean flue gas is released from the top of the absorber via conduit 3. The $CO_2$-rich solution containing the compound of formula (I) is conducted through a pipe 4 to a desorber column 6 via a heat exchanger 5. In the desorber column 6, the $CO_2$-rich solution containing the compound of formula (I) is heated to reverse the absorption reaction. Typical pressure and temperature conditions in the desorber are 0.4-15 atm and 75 to 200° C. $CO_2$ and moisture is collected from the top of the desorber column via conduit 7. The desorber column is heated by means of a reboiler 9, connected to the desorber by conduits 8 and 10. The heat source of the reboiler is preferably low pressure steam at a temperature of 105-135° C., but to achieve higher temperature conditions in the stripper a higher quality steam is necessary, ie, preferably steam with a temperature 5 to 15 degrees higher than the stripper temperature. The $CO_2$-lean solution containing the compound of formula (I) is then conducted through a pipe 11 to the absorber 2 via the heat exchanger 5. In the heat exchanger 5, sensible heat from the $CO_2$-lean solution containing the compound of formula (I) is used to heat the $CO_2$-rich solution from the absorber.

The desorption process which regenerates the compounds of formula (I) may be carried out be any other suitable method known to the person skilled in the art, such as pressure relieving or stripping treatment.

The process according to the present invention may be conveniently carried out in any suitable absorber, including packed, plate or spray towers. These absorbers are interchangeable to a considerable extent although certain specific conditions may favour one over the other.

In addition to conventional packed, plate or spray towers, specialised absorber towers have been developed to meet specific process requirements. Examples of these specific towers include impingement-plate scrubbers and turbulent contact scrubbers.

The process of the present invention may be carried out in either packed, plate or spray towers, or specialised towers developed to meet specific process requirements, and may contain other peripheral equipment as necessary for optimal process operation. Such peripheral equipment may include but is not limited to an inlet gas separator, a treated gas coalescer, a solvent flash tank, a particulate filter and a carbon bed purifier. The inlet gas flow rate varies according to the size of the equipment but is typically between 5 000 and 25 00 cubic meters per second. The solvent circulation rate is typically between 10 and 40 cubic meters per tonne of $CO_2$. The operating pressure of the absorber is typically between 1 and 100 atm with lower operating pressures being typical of post-combustion $CO_2$ capture and higher operating pressures being typical of natural gas treatment and pre-combustion $CO_2$ capture.

In the process of the present invention, a gas stream containing $CO_2$ at or above atmospheric pressure is contacted with a compound of formula (I) at a temperature at or above ambient temperature, preferably between 30° C. to 60° C., and more preferably between 35° C. to 45° C. to effect absorption of $CO_2$ from the gas stream. Optionally, corrosion inhibitors, scale inhibitors, antifoam agents and/or other additives known to those in the art that may assist in the $CO_2$ capture process of the present invention may be employed.

The following examples are offered to illustrate but not to limit the present invention.

EXAMPLES

Example 1

Reductive Amination

This method may be used for the synthesis of secondary or tertiary amine product from either (1) or (3) below.

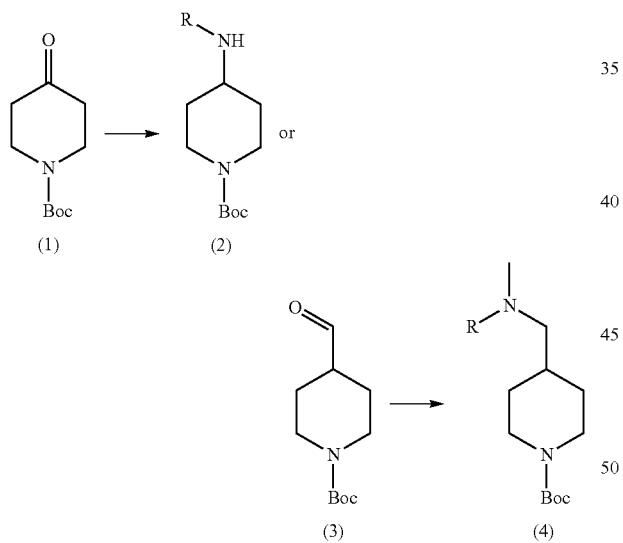

Sodium triacetoxyborohydride, Na(OAc)$_3$BH (60 mmol) was added potionwise to a stirred solution of tert-butyl 4-oxopiperidine-1-carboxylate (1) or 1-Boc-piperidine-4-carboxaldehyde (3) (30 mmol), acetic acid (30 mmole) and corresponding amine, $RNH_2$ or RNHMe, (30 mmole) in dichloromethane (60 ml). The reaction was stirred under nitrogen at room temperature overnight. The reaction was then quenched by the careful addition of $H_2O$ or 1M NaOH (60 mL). The pH of the mixture was adjusted to basic (~pH 10) by the careful addition of solid NaOH and the mixture was stirred for 15-30 min. The organic phase was separated and the aqueous phase was extracted with dichloromethane (2×60 mL). The combined organic phase was washed with $H_2O$ (2×60 mL) and dried by $K_2CO_3$ or filtration through phase separation paper. Removal of the solvent under vacuum gave the product in excellent yield.

NOTE—the amine hydrochloride salt may be used in the reaction. If the amine hydrochloride salt is used, one equivalent of triethylamine ($Et_3N$) is used instead of acetic acid.

A detailed description of this method is provided in Ahmed F. Abdel-Magid, Kenneth G. Carson, Bruce D. Harris, Cynthia A. Maryanoff, and Rekha D. Shah; *Journal of Organic Chemistry*, 1996, 61(11) 3849-3862.

Example 2

Hydrogenation

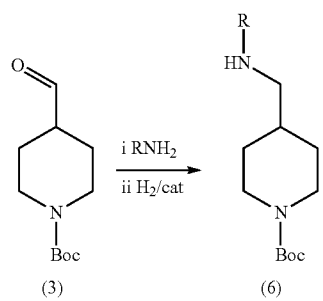

The corresponding amine (30 mmol) was added to a solution of 1-Boc-piperidine-4-carboxaldehyde (3) (30 mmol) in EtOH (40 ml) followed by 10% Pd/C (50% in $H_2O$, 0.3 g). The reaction was processed under a hydrogen atmosphere (40 psi) at room temperature until gas uptake finished and reaction completed (~2-3 hours). The reaction mixture was filtered through celite and the filtrate was evaporated to dryness to give product (6) in excellent yield.

Note: The amine.HCl salt may be used in the reaction. When the amine HCl salt was used an equivalent amount of triethylamine was added. After the above work-up of the reaction, TEA.HCl salt was removed via a partition of dichloromethane-$H_2O$ followed by washing with 5% $Na_2CO_3$. The organic phase was dried (phase separation paper filtration of $K_2CO_3$) and concentrated under vacuum to give the product.

A detailed description of this method is provided in WO 2007/018461.

Example 3

Reductive Amination

The following synthesis of amines (5) and (4) start with amines (2) and (6). The synthesis of amine (2) is provided in Example 1 and the synthesis of amine (6) in Example 2.

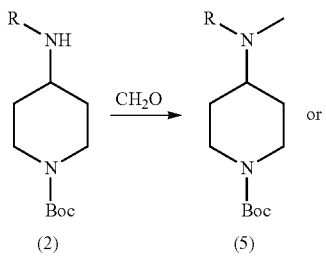

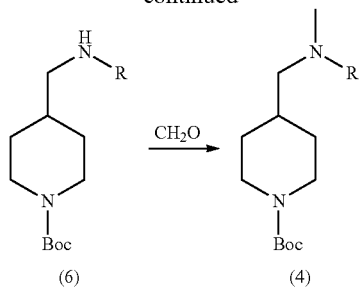

To a solution of amine (2 or 6) (30 mmole) in dichloromethane (200 mL) was added aqueous formaldehyde (37% in H$_2$O, 12.2 mL) followed by sodium triacetoxyborohydride (90 mmol) and AcOH (40 ml). The reaction mixture was stirred under N$_2$ overnight at room temperature. The reaction was quenched by the addition of H$_2$O or 1M NaOH (100 mL). The pH of the mixture was adjusted to basic (~pH 10) by the careful addition of solid NaOH. The organic phase was separated and the aqueous phase was extracted with dichloromethane (2×60 mL). The combined organic phase was washed with H$_2$O (2×60 mL) and dried by K$_2$CO$_3$ or a filtration through phase separation paper. Removal of the solvent under vacuum gave the product (5 or 4) in excellent yield.

A detailed description of this method is provided in Kazuhiro Yokoyama, Noriko Ishikawa, Susumu Igarashi, et al; *Bioorganic & Medicinal Chemistry*, 16 2008, 7968-7974.

Example 4

Alkylation

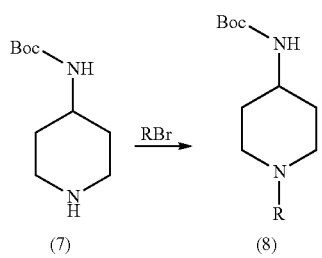

Alkylbromide (49.5 mmol) was added to a stirred suspension of 4-(Boc-amino)-piperidine (7) (45 mmol) and K$_2$CO$_3$ (264 mmol) in acetonitrile (450 ml). The reaction mixture was heated at reflux for 3 hours and then cooled to room temperature. K$_2$CO$_3$ was removed by filtration and the filtrate was concentrated under vacuum to dryness. The residue was dissolved in dichloromethane (90 ml) and water (90 mL) was added. The mixture was stirred and the pH of the mixture was adjusted to pH 10 with NaOH. The organic phase was separated and aqueous phase was extracted with dichloromethane (2×60 mL). The combined organic phase was washed with H$_2$O (2×90 ml) and dried by K$_2$CO$_3$ or a filtration through phase separation paper. Removal of the solvent under vacuum gave product (8) in excellent yield.

Note: the reaction may use an alkylchloride rather than an alkylbromide. If an alkylchloride is used a small quantity of KI was added.

A detailed description of this method is provided in Tien Q. Pham, Ivan Greguric, Xiang Liu, Paula Berghofer, Patrice Ballantyne, Janette Chapman, Filomena Mattner, Branko Dikic, Timothy Jackson, Christian Loc'h, and Andrew Katsifis; *Journal of Medicinal Chemistry*, 2007, 50 (15), 3561-3572.

Example 5

Boc-Deprotection Via Ion-Exchange Resin

Amberlyst 15 resin was used in the Boc-deprotection. The amount of resin used was calculated based on the number of amino groups in the amine molecules. The ratio is 5:1 molar equivalents of resin to each amino-group in the product. Hence, this molar ratio is 10:1 in the case of diamines and 15:1 in the case of tri-amines.

A very slow dropwise flow rate is critical in all operations involved in resin washing or rinsing to achieve complete deprotection and quantitative or near quantitative yield.

The Boc-protected amine (2, 4, 5, 6 or 8) was dissolved in an amount THF that is sufficient to just cover the resin and the solution was added to the resin. The mixture was heated at gentle reflux overnight without stirring. An aliquot of supernatant was evaporate to dryness and analyse by $^1$H NMR to confirm all amine bound to resin. Resin was transferred to a glass column and drained, and then wash with 1× bed volume of THF at a very slow flow rate.

The amine was released from the resin using 2M MeNH$_2$/EtOH (33%, ~8M). An equal molar quantity of MeNH$_2$ with respect to the resin loading was used. The resin was then washed with 1 bed volume of EtOH. In the case of aminoacid derivatives, alcohol was avoided and an aqueous Me$_3$N/H$_2$O solution (45%, ~7.6M) was used to release the amine followed by washing with H$_2$O (1 bed volume). The combined filtrates were concentrated to dryness to yield the free amine.

The resin was regenerated by washing with 3M HCl in MeOH/H$_2$O (1:1) (≥1 eq with respect to resin), water (1-2 bed volumes) followed by MeOH (1 bed volume), and then dichloromethane (1 bed volume). The clean resin was finally dried under N$_2$ or vacuum.

A detailed description of this method is provided in Yun-Shan Liu, Cunxiang Zhao, David E. Bergbreiter, and Daniel Romo; *Journal of Organic Chemistry*, 1998, 63, 3471-3473.

Example 6

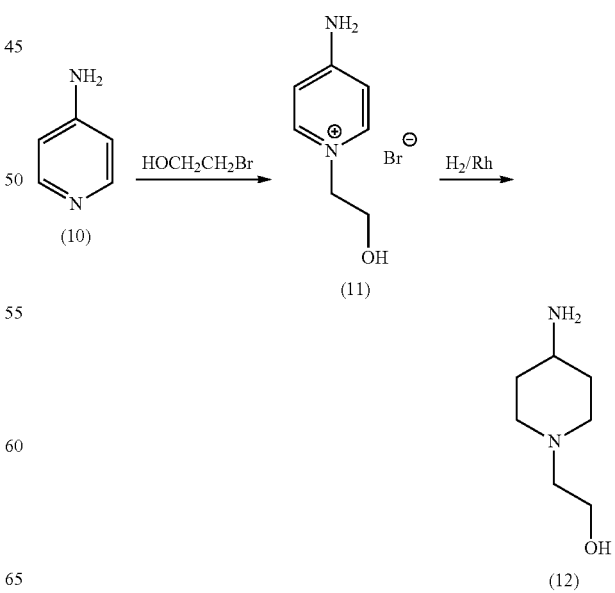

Step 1

2-Hydroxyethylene bromide (9.1 ml, 128 mmol) was added to a solution of 4-aminopyridine (10) (10 g, 106 mmol) in toluene (260 ml). The reaction was heated at reflux for 3.5 hours with stirring and then cooled to room temperature. The formed oil became solid upon cooling. The suspension was filtered and the solid was washed with toluene. The product (11) (22.7 g) was obtained as a pale brown solid at 98% yield.

Note: An alkylchloride or an ω-hydroxy-alkyl chloride is also suitable as a replacement for the bromide compounds in this method.

Step 2

Metallic sodium (1.3 g, 56 mmol) was added slowly to cold MeOH (50 ml) with stirring under nitrogen. The prepared mixture of NaOMe/MeOH was transferred to the hydrogenation vessel and pyridium bromide salt (11) (11.1 g, 51 mmol) obtained from the above reaction was added to the reaction mixture followed by 5% rhodium on charcoal (1.1 g, 10% w/w). The reaction was processed under hydrogen atmosphere (140 psi) at 60° C. overnight. The reaction mixture was filtered through Celite and washed with MeOH (100 mL).

The filtrate was concentrated under vacuum to dryness to confirm complete recovery. The residue was redissolved in MeOH (150 mL) and poured over Amberlyst 15 resin (106 g, 50 mmol). The mixture was heated at gentle reflux without stirring overnight. The resin was transferred to a column and washed with MeOH (150 mL). The amine was released from the resin by using 33% MeNH$_2$/EtOH (63 mL, ~0.5 mol) in EtOH (190 mL) and further washed with EtOH (150 mL). Removal of the solvent of the combined ethanolic fractions gave 5.04 g of clear golden oil (69%). Analysis of $^1$H and $^{23}$Na NMR showed the desired product (12) free from sodium salt.

The product may also be collected by fractional distillation (collected at 122° C./1.0 mbar).

A detailed description of this method is provided in a) Gordon N. Walker, Miriam Ann Moore and Barbara N. Weaver; *Journal of Organic Chemistry*, 1961, 26 (8), 2740-2747; b) Tatsuya Ito, Tomomi Ikemoto, Yasushi Isogami, Hiroki Wada, Misayo Sera, Yukio Mizuno, and Mitsuhiro Wakimasu; *Org. Proc. Res. Dev.*, 2002, 6 (3), 238-241; c) ASTRAZENECA AB, Patent: WO2009/35407 A1, 2009; Location in patent: Page/Page column 10; 21.

Example 7

Synthesis of 4-amino-1-piperidineethanol

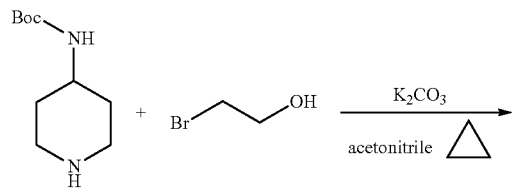

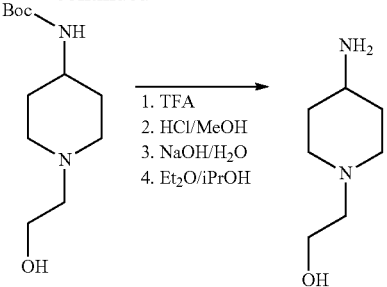

4-(N-Boc amino)-1-piperidineethanol 4-(N-Boc amino)-1-piperidine (10 g, 50 mmol), bromoethanol (7.1 mL, 100 mmol) and K$_2$CO$_3$ (55.2 g, 400 mmol) in acetonitrile (200 mL) were heated at reflux for 5 h. The K$_2$CO$_3$ was filtered off and the acetonitrile was evaporated to dryness (reduced pressure). The resulting residue was dissolved in dichloromethane (100 mL) and H$_2$O (100 mL) was added. The mixture was stirred vigorously and then the phases were allowed to separate, the pH of the aqueous phase was tested (>pH 10, adjust with potassium hydroxide if necessary). The aqueous phase was removed and extracted with dichloromethane (2×100 mL). The combined organic phases were washed with H$_2$O (2×100 mL) and sat. NaCl (100 mL), dried over Na$_2$SO$_4$, filtered and evaporated to dryness (reduced pressure). The product was purified by dry column vacuum chromatography (DCVC) (Pedersen et al.) eluting with methanol/dichloromethane/ethyl acetate (2:9:9), to yield 7.1 g of a golden oil (58% yield) which crystallised on standing to give off-white crystals. $^1$H NMR (CDCl$_3$, 400 MHz) δ 4.43 (br s, 1H), 3.58 (t, J=4.5, 2H), 3.48 (br s, 1H), 2.90-2.78 (m, 2H), 2.51 (t, J=5.4, 2H), 2.24-2.12 (m, 2H), 1.99-1.88 (m, 2H), 1.44 (s, 9H), 1.44-1.35 (m, 2H, superimposed).

4-amino-1-piperidineethanol

The 4-(N-Boc amino)-1-piperidineethanol (13 g, 53.2 mmol) was treated with TFA (26 mL) for 90 mL. The TFA was removed (reduced pressure) and the TEA salt was converted to the HCl salt by treatment with 20% HCl/methanol (130 mL) at ambient temperature for 30 min. The HCl/methanol was evaporated (reduced pressure) and the residue dissolved in H$_2$O (10 mL). The solution was cooled in an ice-bath and NaOH (10M, 35 mL) added to pH >10. The solution was warmed to RT and stirred for 15 min prior to evaporating to dryness. The residue was triturated with ether/isopropanol (2:1), filtered and evaporated to dryness. The trituration process was repeated until no salt was present in the oil (5×) to yield 6.7 g (87%) of an off-white solid.

Example 8

Synthesis of 4-(2-ethanolamino)-piperidine

This method provides a specific example of the method of Example 1 and the method of Example 6.

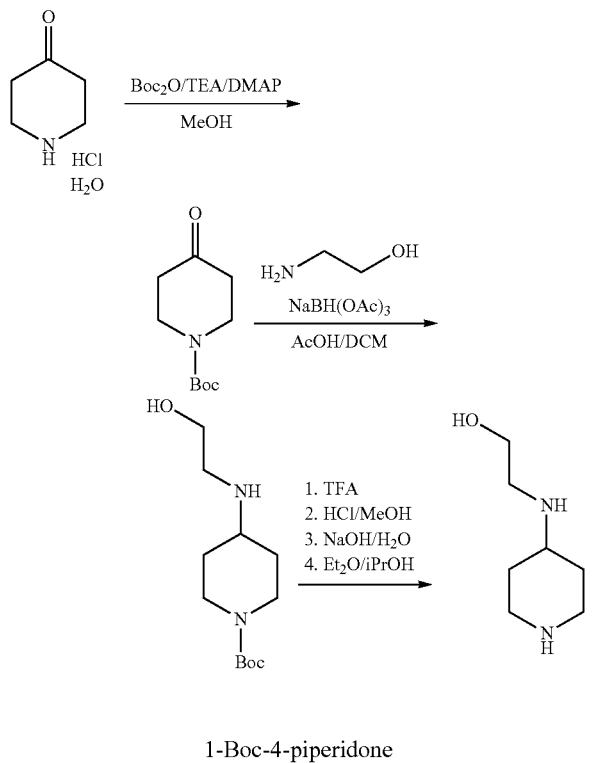

1-Boc-4-piperidone

Triethylamine (19.2 g, 190 mmol) was added to a stirring solution of 4-piperidone monohydrate hydrochloride (20.0 g, 131 mmol) in methanol (300 mL) and stirred for 5 min. Boc$_2$O (34 g, 168 mmol) was added in portions over a 5 min period, followed by DMAP (0.4 g, 3 mmol). The solution was stirred at ambient temperature for 20 h. The methanol was removed under reduced pressure and the crude was dissolved in dichloromethane (100 mL). The organic phase was washed with HCl (2M, 2×70 mL) sat. Na$_2$CO$_3$ (70 mL) and sat NaCl (50 mL), dried over Na$_2$SO$_4$, filtered and evaporated to dryness to yield 1-Boc-4-piperidone as a white solid in quantitative yield. $^1$H NMR (CDCl$_3$ 400 mHz) δ 3.71 (t, J=6.2 Hz, 4H), 2.44 (t, J=6.2 Hz, 4H), 1.49 (s, 9H).

4-(2-ethanolamino)-1-Boc-piperidine

Na(OAc)$_3$BH (40.58 g, 192 mmol) was added slowly to a stirring solution of 1-Boc-4-piperidone (15.25 g, 77 mmol), ethanolamine (4.68 g, 77 mmol) and acetic acid (4.6 g, 77 mmol) in dichloromethane (150 mL) cooled in a water bath under N$_2$ and the solution was stirred at ambient temperature for 18 h. The reaction was quenched by the careful addition of H$_2$O (75 mL) and the mixture stirred for 45 min. The solution was basified to pH 10 by the careful addition of 25% NaOH (~150 mL) and stirred a further 10 min. The phases were allowed to separate and the organic phase was washed with H$_2$O (150 mL) and saturated NaCl (150 mL), dried over Na$_2$SO$_4$, filtered and evaporated to dryness to yield the target (17.49 g, 94%) as a clear oil which crystallised on standing.

$^1$H NMR (CDCl$_3$ 400 mHz) δ 4.02 (br s, 2H), 3.63 (tr, J=5.2 Hz, 2H), 2.88-2.71 (m, 4H), 2.66-2.54 (m, 1H), 1.91-1.79 (m, 2H), 1.44 (s, 9H), 1.31-1.15 (m, 2H).

4-(2-ethanolamino)-piperidine

The 4-(2-ethanolamino)-1-Boc-piperidine (14 g, 57.3 mmol) was treated with TFA (28 mL) for 90 mL. The TFA was removed (reduced pressure) and the TFA salt was converted to the HCl salt by treatment with 20% HCl/methanol (140 mL, 280 mmol HCl) at ambient temperature for 30 min. The HCl/methanol was evaporated (reduced pressure) to yield a white solid in quantitative yield. $^{19}$F NMR (MeOD) confirmed complete conversion to the HCl salt.

The salt was dissolved in H$_2$O (10 mL) and cooled in an ice-bath. NaOH (10M, 35 mL) was added to pH >10. The solution was warmed to RT and stirred for 15 min prior to evaporating to dryness. The residue was triturated with ether/isopropanol (2:1), filtered and evaporated to dryness. The trituration process was repeated until no salt was present in the oil (5×) to yield 7.8 g (95%) of a clear oil which solidified on standing.

Example 9

The test results (shown in the accompanying figures) are a comparison of four compounds within general formula (I) with 4-aminopiperidine in terms of their CO$_2$ absorption at 40° C. (FIG. 2(a)) and CO$_2$ desorption at 90° C. (FIG. 2(b)). These absorption experiments were carried with CO$_2$ gas (99%).

The compounds within the scope of Formula (I) used in this example are as follows:

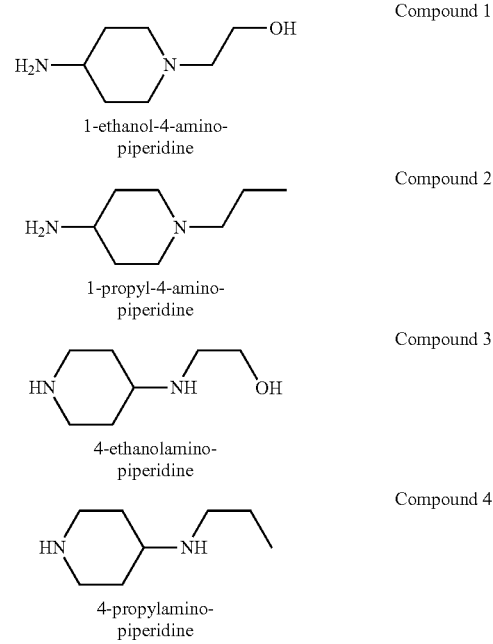

As can be seen from the graphs shown in FIG. 2(a), compounds 1, 2 and 3 have higher capacities for CO$_2$ loading (200%, 180% and 180% on a mol % basis, respectively) than 4-aminopiperidine (155%). 4-Propylaminopiperidine (Compound 4) has a higher CO$_2$ loading in absorption than the result shown in FIG. 2(a) Compound 4 formed a large quantity of bicarbonate solid during its CO$_2$ absorption, which was not able to be measured by $^{13}$C NMR, hence, the real CO$_2$ loading was higher than that illustrated in FIG. 2(a). As can be seen from FIG. 2(a) compounds 1 to 4 have faster or at least similar reaction rates in absorption.

Compounds 1 to 4 also displayed better $CO_2$ release in desorption (FIG. 2(b)). Compounds 1 to 3 desorbed more $CO_2$ (105%, 100% and 86% on a mol % basis, respectively) at moderate temperatures (90° C.), than did 4-aminopiperidine (67%). Again, the desorption yield of Compound 4 could not be accurately measured due to the inability to accurately measure the $CO_2$ loading of the starting material.

The results above indicated that the compounds of Formula (I) may improve $CO_2$ capture capacity ($CO_2$ absorption and desorption) of known systems. The compounds exhibited a more efficient cycle of $CO_2$ absorption-desorption, which may lead to significantly lower the energy consumption in $CO_2$ capture.

These results were also compared with monoethanolamine (MEA) and piperizine (Pz) for their $CO_2$ absorption and desorption. MEA and Pz are commercially available amines used in industry for $CO_2$ capture. Aqueous MEA is used as a $CO_2$ absorber due to its attractive $CO_2$ loading capacity in g $CO_2$/g MEA whilst it's desorption is poor and high energy consumption is required. Pz was claimed widely as a promoter in $CO_2$ absorption by amines, but our study results showed that Pz carbamate was reasonably stable at 90° C., and this limited its capacity as a promoter in $CO_2$ capture at lower energy consumption.

In FIG. 3, $CO_2$ absorption and desorption results for Compounds 1 to 4 and 4-aminopiperidine (2M and 1.7M in one case due to the material availability) were compared with MEA (4M) and piperazine (Pz) (2M). An MEA concentration of 4M was chosen in this comparison to match the total amine/nitrogen concentration of diamines (2×2M).

The results of $CO_2$ absorption at 40° C. are displayed as a ratio of mole of $CO_2$/mole of amine (FIG. 3(a)) and as a ratio of mole of $CO_2$/mole of nitrogen (FIG. 3(c)). The results of desorption at 90° C. are also displayed in the same two ways respectively in FIG. 3(b) and FIG. 3(d). Compounds 1 to 4 as a whole showed better reaction rates for $CO_2$ loading and $CO_2$ release in absorption and desorption. 1-ethanol-4-aminopiperidine (Compound 1), in particular, stood out during this comparison as shown by its highest loading in absorption and largest release of $CO_2$ in desorption. It also had the highest reaction rates in both reactions.

Example 10

$CO_2$ Absorption-Desorption

1. Absorption

An amine solution (2M, 10 mL) was added to a 50 ml jacketed 2-necked pear-shaped flask. The reaction solution was stirred, heated to and maintained at 40° C. with a Ratek Thermoregulator thermostatted bath. The stirring speed, 900 rpm, was kept the same in all absorption and desorption experiments. A condenser was connected to the flask through a Claisen adapter, and an electronic thermometer introduced to monitor the temperature of the amine solution. Hydrated gas of 10% $CO_2$ and 90% $N_2$ was introduced to the amine solution through a PTFE tube (0.71 mm ID, 1.78 mm OD) at a total flow rate of 50 mL/min (controlled via a Bronkhorst High-Tech El-Flow mass flow controller). The loading was processed over night (18 hours). A sample was taken for NMR analysis.

The concentration of MEA used in experiment was 4M. This concentration provided same total concentration of amino-groups to that of 2M diamines.

2. Desorption

After the gas supply was removed, the $CO_2$-rich amine solution obtained from the above absorption was heated at a constant temperature of 90° C. with a Ratek Thermoregulator thermostatted bath. Samples are taken from reaction for NMR analysis at reaction time of 2, 5, 10, 30 and 60 minutes.

3. General Method for Quantitative $^{13}C$ NMR Analysis and Data Processing

NMR samples were placed into a 5 mm (178 mm long, 4.24 mm ID) NMR tube to a height of 40 mm then capped, and an external standard of 1,4-dioxane in a sealed capillary was used in $^{13}C$ NMR analysis ($\delta_C$ 67.18 ppm, calibrated against an external TMS/CDCl$_3$ solution). Relaxation times ($T_1$) of the carbon atoms in the reaction mixture were measured using the standard inversion recovery ("Null") method. The NMR analytical interscan recycle time was chosen as equal to $5 \times T_1$. NMR spectroscopy was performed at 25° C. The molar ratio of $CO_2$-loading to amine was calculated based on integration of carbonyl signals and amine aliphatic carbon signals. The weight loading figure then was calculated from molar ratio results. The accuracy of loadings determined in this manner was estimated to be ±3% for amine concentrations of 4 M. The cyclic capacity is the calculated difference between the maximum and minimum $CO_2$ loading in the process of absorption-desorption cycle.

4. pKa Calculations

Software: SPARC Online Calculator version 4.6—http://archemcalc.com/sparc/

Conditions: 25° C., 0 M ionic strength, aqueous solution.

TABLE 1

$CO_2$ sequestration in 10% $CO_2$ and 90% $N_2$

| Compound | Maximum $CO_2$ loading | | Cyclic capacity in $CO_2$ absorption/ desorption | | pK$_a$ | |
|---|---|---|---|---|---|---|
| | Molar capacity | g/g | Molar capacity | g/g | Amine in the ring | Amine not in the ring |
| [structure] | 1.46 | 0.51 | 0.43 | 0.15 | 10.47 | 10.34 |

TABLE 1-continued

CO₂ sequestration in 10% CO₂ and 90% N₂

| Compound | Maximum CO₂ loading | | Cyclic capacity in CO₂ absorption/ desorption | | pK$_a$ | |
|---|---|---|---|---|---|---|
| | Molar capacity | g/g | Molar capacity | g/g | Amine in the ring | Amine not in the ring |
| HO-CH₂CH₂-NH-(4-piperidyl)-NH | 1.02 | 0.35 | 0.41 | 0.15 | 10.41 | 9.73 |
| HO-(CH₂)₃-NH-(4-piperidyl)-NH | 1.05 | 0.29 | 0.34 | 0.09 | 10.44 | 10.13 |
| HO-(CH₂)₆-NH-(4-piperidyl)-NH | 1.15 | 0.25 | 0.46 | 0.10 | 10.46 | 10.28 |
| (CH₃)₂N-(CH₂)₃-NH-(4-piperidyl)-NH | 1.50 | 0.39 | 0.69 | 0.18 | 10.43 | 9.55 (9.51) |
| CH₃(C₂H₅)N-(4-piperidyl)-NH | 1.30 | 0.40 | 0.43 | 0.13 | 10.47 | 9.68 |
| HO-CH₂CH₂-N(CH₃)-(4-piperidyl)-NH | 1.05 | 0.29 | 0.28 | 0.08 | 10.41 | 9.10 |
| HO-(CH₂)₃-N(CH₃)-(4-piperidyl)-NH | 1.07 | 0.27 | 0.36 | 0.09 | 10.44 | 9.52 |
| HO-(CH₂)₆-N(CH₃)-(4-piperidyl)-NH | 1.01 | 0.21 | 0.47 | 0.10 | 10.46 | 9.15 |
| H₂N-(4-piperidyl)-N-C₂H₅ | 1.14 | 0.39 | 0.46 | 0.16 | 9.68 | 9.99 |
| H₂N-(4-piperidyl)-N-C₃H₇ | 1.17 | 0.36 | 0.61 | 0.19 | 9.70 | 9.99 |
| H₂N-(4-piperidyl)-N-CH₂CH₂OH | 1.02 | 0.31 | 0.45 | 0.14 | 9.11 | 9.92 |
| H₂N-(4-piperidyl)-N-(CH₂)₃OH | 1.00 | 0.28 | 0.35 | 0.10 | 9.52 | 9.96 |
| H₂N-(4-piperidyl)-N-(CH₂)₅OH | 0.95 | 0.21 | 0.56 | 0.12 | 9.15 | 9.98 |
| C₂H₅-NH-CH₂-(4-piperidyl)-NH | 1.58 | 0.49 | 0.38 | 0.12 | 10.65 | 10.58 |

TABLE 1-continued

CO₂ sequestration in 10% CO₂ and 90% N₂

| Compound | Maximum CO₂ loading Molar capacity | g/g | Cyclic capacity in CO₂ absorption/desorption Molar capacity | g/g | pKₐ Amine in the ring | pKₐ Amine not in the ring |
|---|---|---|---|---|---|---|
| HO-CH₂CH₂-NH-CH₂-(4-piperidinyl)NH | 1.24 | 0.38 | 0.35 | 0.10 | 10.62 | 9.97 |
| HO-(CH₂)₆-NH-CH₂-(4-piperidinyl)NH | 0.98 | 0.20 | 0.39 | 0.08 | 10.65 | 10.53 |
| HOOC-CH₂-NH-CH₂-(4-piperidinyl)NH | 0.70 | 0.19 | 0.52 | 0.15 | 10.71 | 9.74 |
| (CH₃)₂N-CH₂-NH-CH₂-(4-piperidinyl)NH | 1.80 | 0.43 | 0.53 | 0.13 | 10.63 | 9.79 (9.53) |
| Et(CH₃)N-CH₂-(4-piperidinyl)NH | 1.26 | 0.41 | 0.52 | 0.19 | 10.65 | 9.93 |
| HO-CH₂CH₂-N(CH₃)-CH₂-(4-piperidinyl)NH | 1.13 | 0.29 | 0.44 | 0.11 | 10.62 | 9.35 |

[a] It has been assumed that the amino acids are in the CH₂COO⁻ form in solution. This yields identical results to the amino acids salts.
[b] The pKₐ of any additional nitrogen in the R-group is given in brackets.

Example 10

This example provides $^1$H NMR data for examples of compounds of Formula (I).

TABLE 2

$^1$H NMR data

| R = | HN-(4-piperidinyl)-NH-R | HN-(4-piperidinyl)-N(CH₃)-R | H₂N-(4-piperidinyl)-N-R | HN-(4-piperidinyl)-CH₂-NH-R | HN-(4-piperidinyl)-CH₂-N(CH₃)-R |
|---|---|---|---|---|---|
| Et | $^1$H NMR in d₄-methanol 3.01, 2H, d b, J12.8 Hz; 2.62, 2H, q, J7.3 Hz; 2.57-2.49, 3H, m; 1.86, 2H, m; 1.22, 2H, ddd, J₁24.1 Hz, J₂12.4 H, J₃4.0 Hz; 1.09, 3H, J7.2 Hz. | $^1$H NMR in d₄-methanol 3.05, 2H, d b, J12.6 Hz; 2.59-2.46, 5H, m; 2.23, 3H, s; 1.77, 2H, d b, J12.8 Hz; 1.41, 2H, ddd, J₁24.6 Hz, J₂12.4 H, J₃4.2 Hz; 1.05, 3H, t, J6.2 Hz. | $^1$H NMR in d₄-methanol 2.91, 2H, d b, J12.5 Hz; 2.59, 1H, m; 2.39, 2H, q, J7.3 Hz; 1.99, 2H, td, J₁12.1 Hz, J₂2.4 Hz; 1.81, 2H, d b, J13.4 Hz; 1.38, 2H, m; 1.07, 3H, J7.3 Hz. | $^1$H NMR in d₄-methanol 2.99, 2H, dt, J₁12.3 Hz, J₂3.0 Hz; 2.58, 2H, q, J7.2 Hz; 2.54, 2H, td, J₁12.4 Hz, J₂2.6 Hz; 2.41, 2H, d, J6.8 Hz; 1.70, 2H, m; 1.60, 1H, m; 1.16-1.05, 2H, m; 1.09, 3H, t, J7.2 Hz. | $^1$H NMR in d₄-methanol 3.04, 2H, dt, J₁12.3 Hz, J₂3.0 Hz; 2.60, 2H, td, J₁12.3 Hz, J₂2.7 Hz; 2.45, 2H, q, J7.3 Hz; 2.23, 3H, s; 2.22, 2H, overlapped; 1.77, 2H, m; 1.68, 1H, m; 1.14, 2H, m; 1.09, 3H, t, J7.2 Hz. |

TABLE 2-continued

¹H NMR data

| R = | 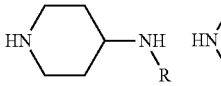 | 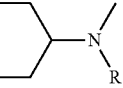 | 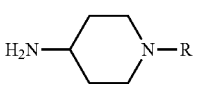 | 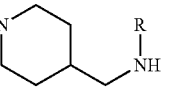 | 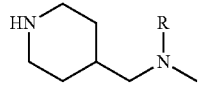 |
|---|---|---|---|---|---|
| $^n$Pr | ¹H NMR in d$_4$-methanol 3.01, 2H, d b, J12.5 Hz; 2.58-2.47, 5H, m; 1.86, 2H, d b, J12.8 Hz; 1.49, 2H, sextet, J7.4 Hz; 1.22, 2H, ddd, J$_1$24.0 Hz, J$_2$12.5 H, J$_3$3.7 Hz; 0.91, 3H, J7.4 Hz. | | ¹H NMR in d$_4$-methanol 2.89, 2H, d b, J12.0 Hz; 2.58, 1H, m; 2.28, 2H, m; 2.00, 2H, td, J$_1$12.0 Hz, J$_2$2.4 Hz; 1.84-1.76, 2H, m; 1.55-1.46, 2H, m; 1.38, 2H, ddd, J$_1$24.0 Hz, J$_2$12.8 Hz, J$_3$3.6 Hz; 0.89, 3H, J7.5 Hz. | | |
| (CH$_2$)$_2$OH | ¹H NMR in d$_4$-methanol 3.74, 2H, t, J5.6 Hz; 3.14, 2H, dt b, J$_1$12.9 Hz, J$_2$3.0 Hz; 2.83, 2H, t, J5.6 Hz; 2.66, 2H, td, J$_1$12.8 Hz, J$_2$2.8 Hz; 2.66, 1H overlapped; 1.99, 2H, d b, J12.8 Hz; 1.36, 2H, ddd, J$_1$23.8 Hz, J$_2$12.6 H, J$_3$4.2 Hz. | ¹H NMR in d$_4$-methanol 3.60, 2H, t, J6.3 Hz; 3.07, 2H, d b, J12.6 Hz; 2.60, 2H, t, J6.3 Hz; 2.58-2.47, 3H, m; 2.28, 3H, s; 1.78, 2H, d b, J12.7 Hz; 1.42, 2H, ddd, J$_1$24.5 Hz, J$_2$12.4 Hz, J$_3$3.9 Hz. | ¹H NMR in d$_4$-methanol 3.65, 2H, t, J6.2 Hz; 2.91, 2H, d b, J12.4 Hz; 2.59, 1H, m; 2.49, 2H, t, J6.1 Hz; 2.09, 2H, td, J$_1$11.9 Hz, J$_2$2.4 Hz; 1.79, 2H, d b, J13.3 Hz; 1.39, 2H, m. | | ¹H NMR in CDCl$_3$ 3.52, 2H, td b, J$_1$5.4 Hz, J$_2$ 0.8 Hz; 3.03, 2H, d b, J12.1 Hz; 2.55, 2H, t b, J12.2 Hz; 2.46, 2H, td b, J$_1$5.5 Hz, J$_2$1.1 Hz; 2.19, 3H, s; 2.21-2.17, 2H overlapped; 1.69, 2H, d b, J12.8 Hz; 1.57, 1H, m; 1.02, 2H, ddd, J$_1$24.4 Hz, J$_1$*12.3 Hz, J$_2$3.8 Hz. |
| (CH$_2$)$_3$OH | ¹H NMR in d$_4$-methanol 3.63, 2H, t, J6.2 Hz; 3.07-2.98, 2H, m; 2.70, 2H, t, J7.3 Hz; 2.60-2.49, 3H, m; 1.94-1.85, 2H, m; 1.75-1.66, 2H, m; 1.31-1.18, 2H, m. ¹³C NMR 61.6, 56.2, 46.0, 44.6, 33.8, 33.3. | ¹H NMR in d$_4$-methanol 3.59, 2H, t, J6.2 Hz; 3.05, 2H, d b, J12.3 Hz; 2.61-2.47, 5H, m; 2.25, 3H, s; 1.77, 2H, d b, J13.2 Hz; 1.72-1.64, 2H, m; 1.42, 2H, ddd, J$_1$24.7 Hz, J$_2$12.5 Hz, J$_3$4.2 Hz. | ¹H NMR in d$_4$-methanol 3.58, 2H, t, J6.2 Hz; 2.91, 2H, d b, J12.4 Hz; 2.60, 1H, m; 2.44, 2H, t, J7.6 Hz; 2.02, 2H, m; 1.81, 2H, d b, J13.0 Hz; 1.71, 2H, m; 1.37, 2H, m. | | |
| (CH$_2$)$_6$OH | | ¹H NMR in d$_4$-methanol 3.52, 2H, t, J6.6 Hz; 3.05, 2H, d b, J12.5 Hz; 2.56-2.42, 5H, m; 2.24, 3H, s; 1.80-1.73, 2H, m; 1.56-1.26, 10H, m. | ¹H NMR in d$_4$-methanol 3.57, 2H, t, J6.6 Hz; 2.95, 2H, d b, J12.3 Hz; 2.66, 1H, m; 2.37, 2H, m; 2.06, 2H, td, J$_1$12.3 Hz, J$_2$2.6 Hz; 1.86, 2H, d b, J12.6 Hz; 1.61-1.51, 4H, m; 1.50-1.32, 6H, m. | | |
| CH$_2$COOH | ¹H NMR in D$_2$O 3.27, 2H, d b, J12.8 Hz; 3.11, 2H, s; 2.83, 2H, t b, J12.8 Hz; 2.71, 1H, m; 1.97, 2H, d b, J13.2 Hz; 1.38, 2H, m. | | | ¹H NMR in D$_2$O 3.25, 2H, d b, J12.8 Hz; 3.05, 2H, s; 2.82, 2H, td, J$_1$12.8 Hz, J$_2$3.0 Hz; 2.40, 2H, d, J6.8 Hz; 1.87-1.79, 2H, m; 1.76-1.64, 1H, m; 1.25, 2H, m | |
| (CH$_2$)$_2$N(CH$_3$)$_2$ | ¹H NMR in d$_4$-methanol 3.02, 2H, d b, J13.1 Hz; 2.70, 2H, t, J6.8 Hz; 2.59-2.50, 2H, m; 2.43, 2H, t, J6.7 Hz; 2.23, 6H, s; 1.91-1.84, 2H, m; 1.23, 2H, m. | | | ¹H NMR in d$_4$-methanol δ 3.00, 2H, m; 2.66, 2H, t, J7.2 Hz; 2.55, 2H, J$_1$12.3 Hz, J$_2$2.1 Hz; 2.47-2.42, 4H, m; 2.23, 6H, s; 1.71, 2H, d b J13.0 Hz; 1.67-1.54, 1H, m; 1.11, 2H, m. | |

REFERENCES

1. Singh, P., Versteeg, G. F., Structure and activity relationships for CO2 regeneration from aqueous amine-based absorbents, *Process Safety Env. Prot.*, 2008, 86, 347-359.
2. Pedersen, D. S, and Rosenbohm, C., *Synthesis*, 2001, 16, 2431-2434

It will be understood that the invention disclosed and defined in this specification extends to all alternative combinations of two or more of the individual features mentioned or evident from the text or drawings. All of these different combinations constitute various alternative aspects of the invention.

The claims defining the invention are as follows:

1. A process for the capture of $CO_2$ from gas streams, the process including contacting a $CO_2$ containing gas stream with a compound including:
   - a primary or non-sterically hindered secondary amine group and
   - at least one tertiary amine or sterically hindered secondary amine group;

wherein the primary or non-sterically hindered secondary amine and the nearest tertiary or sterically hindered secondary amine group are separated by a carbon chain including 3 or 4 carbon atoms and wherein the compound is a compound of Formula (I)

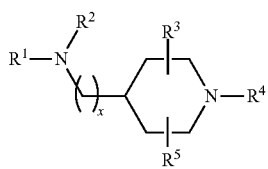

(I)

wherein $R^1$ is represented by hydrogen, $C_2$ to $C_6$ alkanol or $C_1$ to $C_6$ alkyl;

$R^2$ is represented by hydrogen, $C_1$ to $C_6$ alkyl, $C_2$ to $C_6$ alkanol, $—(CH_2)_n—NR_6R_7$, $—(CH_2)_p—COOH$, $—(CH_2)_pCOOQ$, $—(CH_2)_p$-heterocyclic ring containing one to four heteroatoms independently selected from nitrogen, oxygen and sulphur;

$R^3$ and $R^5$ are independently selected from hydrogen, $C_1$ to $C_4$ alkyl, $C_2$ to $C_6$ alkanol, $—(CH_2)_n—NR^8R^9$;

$R^4$ is represented by hydrogen, $C_1$ to $C_6$ alkyl, $C_2$ to $C_6$ alkanol, $—(CH_2)_n—NR_6R_7$, $—(CH_2)_p—COOH$, $—(CH_2)_pCOOQ$, $—(CH_2)_p—SO_3H$, $—(CH_2)_pSO_3Q$, $—(CH_2)_p—PO_3H_2$, $—(CH_2)_pPO_3Q_s$, $—(CH_2)_p$-heterocyclic ring containing one to four heteroatoms independently selected from nitrogen, oxygen and sulphur;

x 0 or 1;

n is 2 to 6;

p is 1 to 6;

Q is hydrogen, a metal ion or $R^{16}R^{17}R^{18}R^{19}N^+$;

s is 1 or 2

$R^6$ and $R^7$ are independently selected from hydrogen, alkyl, alkanol, alkylamine or $R^6$ and $R^7$ together with the nitrogen atom to which they are attached form a ring structure $R^8$ and $R^9$ are independently selected from $C_1$ to $C_6$ alkyl, $C_2$ to $C_6$ alkanol, $C_2$ to $C_6$ alkylamine, $—(CH_2)_n—NR_6R_7$, $—(CH_2)_p—COOH$, $—(CH_2)_pCOOQ$, $—(CH_2)_p—SO_3H$, $—(CH_2)_pSO_3Q$, $—(CH_2)_p—PO_3H_2$, $—(CH_2)_pPO_3Q_s$, or $R^8$ and $R^9$ together with the nitrogen atom to which they are attached form a ring structure; and $R^{16}$, $R^{17}$, $R^{18}$ and $R^{19}$ are independently selected from hydrogen or alkyl;

with the proviso that when $R^4$ is hydrogen, $R^1$ and/or $R^2$ is not hydrogen;

when $R^4$ is not hydrogen, $R^1$ and/or $R^2$ is hydrogen;

when $R^4$ and $R^1$ are both hydrogen, $R^2$ is not methyl; and when $R^4$ and $R^2$ are both hydrogen, $R^1$ is not methyl.

2. A process according to claim 1 wherein the compound is a compound of formula (I), wherein:

$R^1$ is represented by hydrogen or $C_1$ alkyl;

$R^2$ is represented by hydrogen, $—CH_2CH_3$, $—CH_2CH_2CH_3$, $—(CH_2)_2OH$, $—(CH_2)_3OH$, $—(CH_2)_6OH$, $—CH_2COOH$, $—CH_2COONa$, $—CH_2COOK$, $—(CH_2)_2N(CH_3)_2$, $—(CH_2)_2N(CH_2CH_2)_2O$, $—(CH_2)_2N(CH_2CH_2)_2S$, $—CH_2(5\text{-imidazole})$ or $—(CH_2)_2(5\text{-imidazole})$;

$R^3$ is represented by hydrogen;

$R^4$ is represented by hydrogen, $—CH_2CH_3$, $—CH_2CH_2CH_3$, $—(CH_2)_2OH$, $—(CH_2)_3OH$, $—(CH_2)_6OH$, $—CH_2COOH$, $—CH_2COONa$, $—CH_2COOK$, $—(CH_2)_2N(CH_3)_2$, $—(CH_2)_2N(CH_2CH_2)_2O$, $—(CH_2)_2N(CH_2CH_2)_2S$, $—CH_2(5\text{-imidazole})$ or $—(CH_2)_2(5\text{-imidazole})$; and $R^5$ is represented by hydrogen;

with the proviso that when $R^4$ is hydrogen, $R^2$ is not hydrogen;

when $R^2$ is hydrogen, $R^4$ is not hydrogen; and when $R^2$ is hydrogen, $R^1$ is hydrogen and x is 0.

3. A process according to claim 2 wherein the compound is a compound of formula (I), wherein:

$R^1$ is represented by hydrogen or $C_1$ alkyl;

$R^2$ is represented by hydrogen, $—CH_2CH_3$, $—CH_2CH_2CH_3$, $—(CH_2)_2OH$, $—(CH_2)_3OH$, $—(CH_2)_6OH$, $—CH_2COOH$, $—CH_2COONa$, $—CH_2COOK$, $—(CH_2)_2N(CH_3)_2$, $—(CH_2)_2N(CH_2CH_2)_2O$, $—(CH_2)_2N(CH_2CH_2)_2S$, $—CH_2(5\text{-imidazole})$ or $—(CH_2)_2(5\text{-imidazole})$;

$R^3$ is represented by hydrogen;

$R^4$ is represented by hydrogen; and $R^5$ is represented by hydrogen.

4. A process according to claim 2 wherein the compound is a compound of formula (I), wherein:

x is 0;

$R^1$ is represented by hydrogen;

$R^2$ is represented by hydrogen;

$R^3$ is represented by hydrogen;

$R^4$ is represented by hydrogen, $—CH_2CH_3$, $—CH_2CH_2CH_3$, $—(CH_2)_2OH$, $—(CH_2)_3OH$, $—(CH_2)_6OH$, $—CH_2COOH$, $—CH_2COONa$, $—CH_2COOK$, $—(CH_2)_2N(CH_3)_2$, $—(CH_2)_2N(CH_2CH_2)_2O$, $—(CH_2)_2N(CH_2CH_2)_2S$, $—CH_2(5\text{-imidazole})$ or $—(CH_2)_2(5\text{-imidazole})$; and $R^5$ is represented by hydrogen.

5. A process according to claim 3 wherein the compound is a compound of formula (I), wherein:

$R^1$ is represented by hydrogen or $C_1$ alkyl;

$R^2$ is represented by $—CH_2CH_3$, $—CH_2CH_2CH_3$, $—(CH_2)_2OH$, $—(CH_2)_3OH$, $—(CH_2)_6OH$, $—CH_2COOH$ or $—(CH_2)_2N(CH_3)_2$;

$R^3$ is represented by hydrogen;

$R^4$ is represented by hydrogen; and $R^5$ is represented by hydrogen.

6. A process according to claim 4 wherein the compound is a compound of formula (I), wherein:

$R^1$ is represented by hydrogen;

$R^2$ is represented by hydrogen;

$R^3$ is represented by hydrogen;

R⁴ is represented by —CH₂CH₃, —CH₂CH₂CH₃, —(CH₂)₂OH, —(CH₂)₃OH or —(CH₂)₆OH; and
R⁵ is represented by hydrogen.

7. A process according to claim 2 wherein the compound is a compound of formula (I), wherein:
R¹ is represented by hydrogen or C₁ alkyl;
R² is represented by hydrogen, —CH₂CH₃, —CH₂CH₂CH₃ or —(CH₂)₂N(CH₃)₂;
R³ is represented by hydrogen;
R⁴ is represented by hydrogen, —CH₂CH₃, —CH₂CH₂CH₃ or —(CH₂)₂N(CH₃)₂; and
R⁵ is represented by hydrogen;
with the proviso that when R⁴ is hydrogen, R² is not hydrogen;
when R² is hydrogen, R⁴ is not hydrogen; and
when R² is hydrogen, R¹ is hydrogen and x is 0.

8. A process according to claim 2 wherein the compound is selected from the group consisting of:

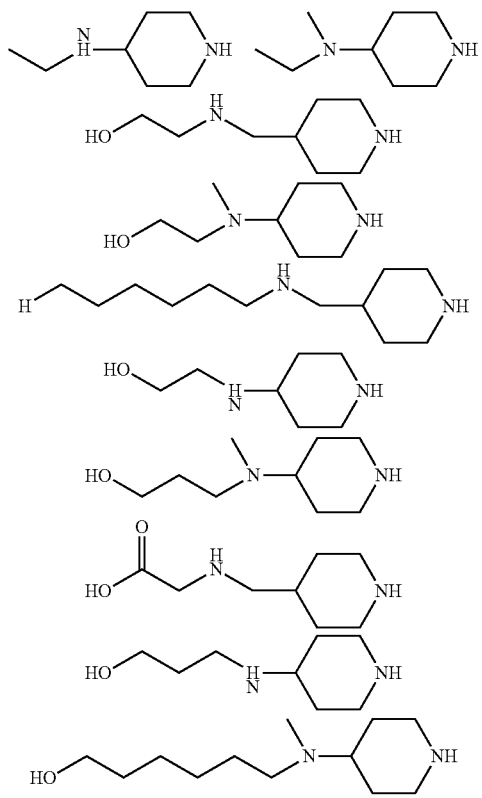

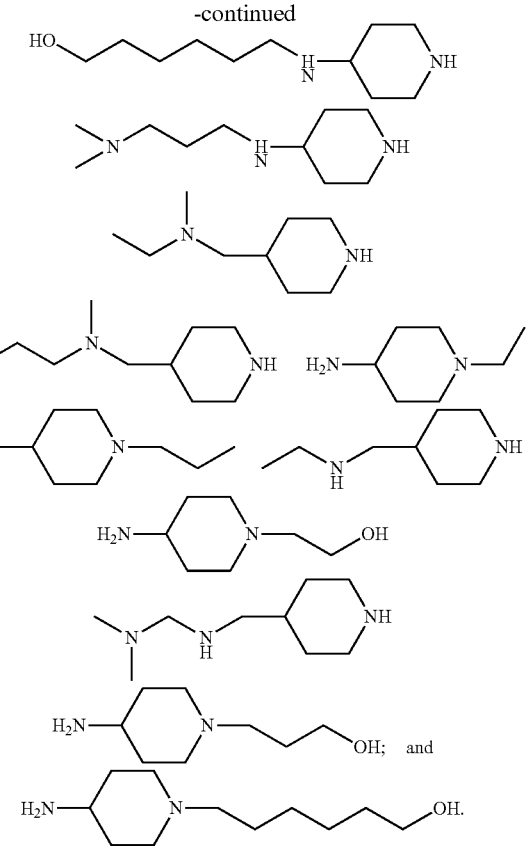

9. A process according to claim 2 wherein the compound is selected from the group consisting of:

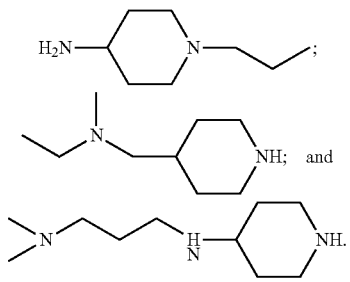

* * * * *